US006726718B1

(12) United States Patent
Carlyle et al.

(10) Patent No.: US 6,726,718 B1
(45) Date of Patent: Apr. 27, 2004

(54) MEDICAL ARTICLES PREPARED FOR CELL ADHESION

(75) Inventors: Wenda C. Carlyle, Petaluma, CA (US); Avrom M. Brendzel, Roseville, MN (US)

(73) Assignee: St. Jude Medical, Inc.

( * ) Notice: Subject to any disclaimer, the term of this patent is extended or adjusted under 35 U.S.C. 154(b) by 0 days.

(21) Appl. No.: 09/459,451

(22) Filed: Dec. 13, 1999

(51) Int. Cl.⁷ .................................................. A61F 2/24
(52) U.S. Cl. ................ 623/2.42; 623/23.56; 623/23.57; 623/23.76
(58) Field of Search .......................... 623/23.56, 23.29, 623/23.57, 23.76, 2.42; 427/2.24

(56) References Cited

U.S. PATENT DOCUMENTS

| | | | |
|---|---|---|---|
| 3,685,059 A | | 8/1972 | Bokros et al. ...................... 3/1 |
| 4,620,327 A | | 11/1986 | Caplan et al. |
| 4,648,881 A | | 3/1987 | Carpentier et al. ............ 623/11 |
| 4,798,611 A | | 1/1989 | Freeman, Jr. ................. 623/66 |
| 5,002,582 A | | 3/1991 | Guire et al. .................... 623/11 |
| 5,080,668 A | | 1/1992 | Bolz et al. ....................... 623/2 |
| 5,147,400 A | | 9/1992 | Kaplan et al. ................. 623/11 |
| 5,147,514 A | | 9/1992 | Mechanic .............. 204/157.68 |
| 5,192,312 A | | 3/1993 | Orton ........................... 623/11 |
| 5,194,596 A | | 3/1993 | Tischer et al. .............. 530/399 |
| 5,607,469 A | | 3/1997 | Frey ................................ 623/2 |
| 5,607,918 A | | 3/1997 | Eriksson et al. .............. 514/12 |
| 5,613,982 A | * | 3/1997 | Goldstein ..................... 623/11 |
| 5,648,301 A | * | 7/1997 | Ducheyne et al. ............ 501/39 |
| 5,728,152 A | * | 3/1998 | Mirsch, II et al. .............. 623/2 |
| 5,728,420 A | * | 3/1998 | Keogh ........................ 427/2.12 |
| 5,759,205 A | * | 6/1998 | Valentini ..................... 623/16 |
| 5,811,151 A | * | 9/1998 | Hendricks et al. .......... 427/2.24 |
| 5,817,327 A | | 10/1998 | Ducheyne et al. |
| 5,899,939 A | * | 5/1999 | Boyce et al. .................. 623/16 |
| 6,013,106 A | * | 1/2000 | Tweden et al. ............... 623/66 |
| 6,033,719 A | * | 3/2000 | Keogh ........................ 427/2.12 |
| 6,413,538 B1 | * | 7/2002 | Garcia et al. ................ 424/423 |

FOREIGN PATENT DOCUMENTS

| | | | |
|---|---|---|---|
| EP | 0 476 983 A1 | 3/1992 | |
| EP | 0 506 477 A1 | 9/1992 | |
| EP | 0 550 296 A2 | 7/1993 | |
| EP | 0 616 814 A1 | 9/1994 | |
| EP | 0 742 020 A2 | 11/1996 | |
| US | WO-99/37337 | * 7/1999 | ........... A61L/27/00 |
| WO | WO 86/00526 | 1/1986 | |
| WO | WO 95/24473 | 9/1995 | |
| WO | 95/31944 | 11/1995 | |
| WO | 98/52619 | 11/1998 | |
| WO | 99/37337 | 7/1999 | |

OTHER PUBLICATIONS

"Endothelialization of Mechanical Heart Valves In Vitro with Cultured Adult Human Cells", Bengtsson et al., The Journal of Heart Valve Disease, vol. 2, No. 3, pp. 352–356, May 1993.*

(List continued on next page.)

*Primary Examiner*—David H. Willse
*Assistant Examiner*—Javier G. Blanco
(74) *Attorney, Agent, or Firm*—Altera Law Group, LLC; Hallie A. Finucane

(57) ABSTRACT

A prosthesis is formed from a biocompatible material having one or more associated cell adhesion stimulating proteins. The biocompatible material can be a ceramic material or a carbon coated material. The cell adhesion stimulating protein can be a structural protein or a polypeptide growth factor, such as vascular endothelial growth factor. Viable cells can be adhered in vivo or in vitro to the biocompatible material with the cell adhesion stimulating protein.

35 Claims, 16 Drawing Sheets

OTHER PUBLICATIONS

"Accelerated Endothelialization by Local Delivery of Recombinant Human Vascular Endothelial Growth Factor Reduces In-Stent Intimal Formation" by, Bell et al., Biochemical and Bio Physical Research Communication 235, 311–316 (1997).

"Conditional Switching of Vascular Endothelial Growth Factor (VEGF) Expression in Tumors: Induction of Endothelial Cell Shedding and Regression of Hemangioblastoma–like Vessels by VEGF Withdrawal" by, Benjamin et al., Proc. Natl. Acad. Sci. USA, vol. 94. pp. 8761–8766, Aug. 1997, Medical Sciences.

"Endothelialization of Mechanical Hear Valves In Vitro with Cultured Adult Human, Cells" by, Bengtsson et al., The Journal of Heart Valve Disease, vol. 2, No. 3, pp. 352–356, May 1993.

"Passivation of Metallic Stents After Arterial Gene Transfer of phVEGF$_{165}$Inhibits Thrombus Formation and Intimal Thickening" by, VanBelle et al., JACC vol. 29, No. 6, May 1997:1371–1379.

"Stent Endothelialization: Time Course, Impact of Local Catheter Deliver, Feasibility of Recombinant Protein Administration, and Response to Cytokine Expedition" by, Van Belle et al., Circulation, vol. 95. No. 2 Jan. 21, 1997, pp. 438–448.

"Stimulation of Endothelial Cell Migration by Vascular Permeability Factor/Vascular Endothelial Growth Factor through Cooperative Mechanisms Involving the $\alpha_v\beta_3$ Integrin, Osteopontin, and Thrombin" by, Senger et al., American Journal of Pathology, vol. 149, No. 1, Jul. 1996, pp. 293–305.

"Synergistic Effect of Vascular Endothelial Growth Factor and Basic Fibroblast Growth Factor on Angiogenesis in Vivo" by, Asahara et al., Supplemental II Circulation vol. 92, No. 9, Nov. 1, 1995, pp. 365–371.

"Vascular Endothelial Growth Factor and Heparin in a Biologic Glue Promotes Human Aortic Endothelial Cell Proliferation with Aortic Smooth Muscle Cell Inhibition" by, Weatherford et al., Surgery, vol. 120, No. 2, pp. 433–439 (Aug. 1996).

"Vascular Endothelial Growth Factor Inhibits Endothelial Cell Apoptosis Induced by Tumor Necrosis Factor $\alpha$: Balance Between Growth and Death Signals" by, Spyridopoulos et al., J. Mol. Cell. Cardiol., vol. 29, 1321–1330 (1997).

"Vascular Permeability Factor/Vascular Endothelial Growth Factor Inhibits Anchorage–Disruption–Induced Apoptosis in Microvessel Endothelial Cells by Inducing Scaffold Formation", by Watanabe et al., Experimental Cell Research 233, pp. 340–349 (1997).

"Vascular Permeability Factor/Vascular Endothelial Growth Factor (VPF/VEGF) Delays and Induces Escape from Senescence in Human Dermal Microvascular Endothelial Cells", by Watanabe et al., Oncogene (1997) 14, 2025–2032.

* cited by examiner

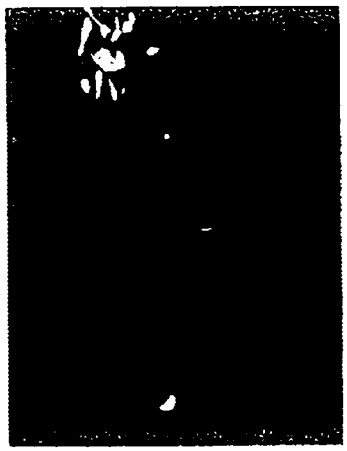
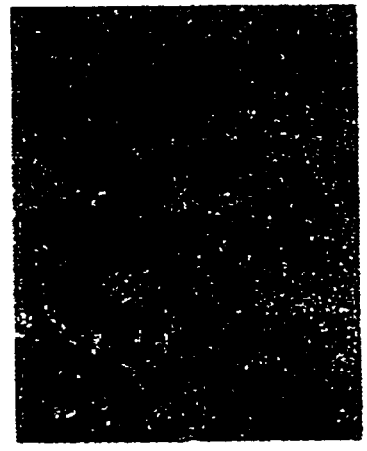

Fig. 13

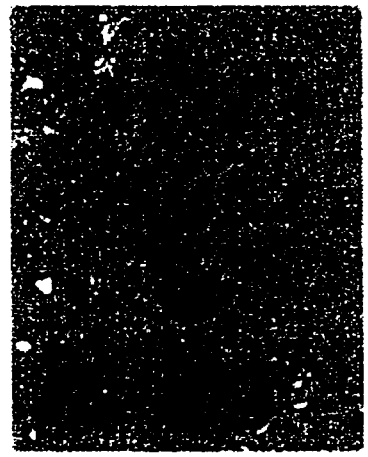
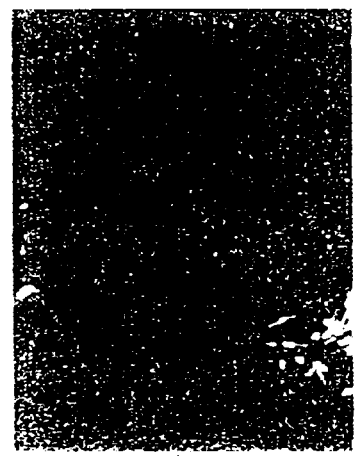
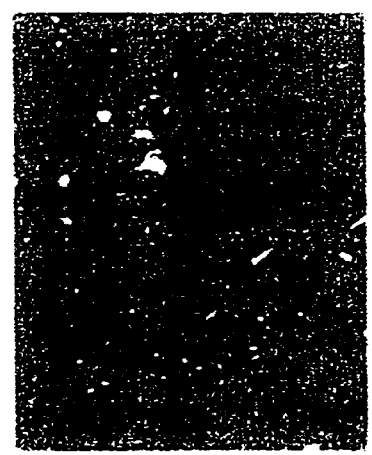
Fig. 14

Fig. 15
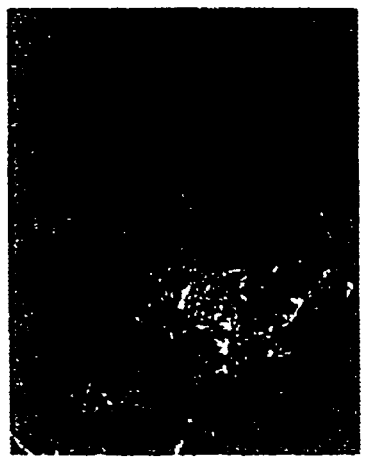

MEDICAL ARTICLES PREPARED FOR CELL ADHESION

FIELD OF THE INVENTION

The invention relates to medical articles having components that have been modified with a compound that stimulates cell adhesion, such as a structural protein or a polypeptide growth factor. The invention further relates to methods for producing these medical articles.

BACKGROUND OF THE INVENTION

Prostheses, i.e., prosthetic devices, are used to repair or replace damaged or diseased organs, tissues and other structures in humans and animals. Prostheses must be generally biocompatible since they are typically implanted for extended periods of time. Prostheses can be constructed from natural materials such as tissue, synthetic materials or a combination thereof. For example, prostheses, such as mechanical heart valve prostheses, are manufactured from biocompatible metals and other materials, such as pyrolytic carbon coated graphite and polyester. Mechanical heart valves generally include an occluder that pivots within an orifice ring, through which blood flows. Pivoting of the occluder opens and closes the valve.

Although mechanical heart valves have the advantage of proven durability through decades of use, they are associated with a potential for blood clotting on or around the prosthetic valve. Blood clotting can lead to acute or subacute closure of the valve or associated blood vessel. For this reason, patients with implanted mechanical heart valves remain on anticoagulants after implantation of the valve. Anticoagulants impart a potential risk of significant bleeding complications and cannot be taken safely by certain individuals. Occluders and orifice rings of mechanical heart valves can be formed from materials, such as pyrolytic carbon, that reduce the risk of blood clotting by the nature of their relative thromboresistance.

In addition to heart valve prostheses formed with rigid occluders, heart valve prostheses can be constructed from tissue or flexible polymer materials. Thrombosis and calcification are concerns associated with polymer heart valves. Tissue-derived prosthetic heart valves generally have blood flow characteristics and surface properties that provide a high degree of thromboresistance without the need for anticoagulant therapy. Therefore, thrombosis or thromboembolism and bleeding complications are less likely to occur than with mechanical heart valves. Unfortunately, prosthetic tissue heart valves are limited by a tendency to fail beginning about seven to ten years following implantation. Valve degeneration is particularly rapid in young patients and during pregnancy. Calcification, i.e., the deposition of calcium salts, especially calcium phosphate (hydroxyapatite), appears to be a major cause of degeneration. Flexible polymer heart valves also tend to fail due to calcification and subsequent degeneration.

Native heart valve tissue with viable cells has natural protection against calcification. Endothelial cells that coat the blood contacting surfaces of a native valve provide a barrier against calcification. These cells also protect against infection and provide active thromboresistance.

SUMMARY OF THE INVENTION

In a first aspect, the invention pertains to a medical article suitable for contacting a patient's bodily fluids. The medical article includes a biocompatible material and at least one cell adhesion stimulating protein associated with the biocompatible material. The biocompatible material includes a ceramic material over at least part of its surface.

In another aspect, the invention pertains to a method for producing a medical article suitable for contact with a patient's bodily fluids. The method includes the adhering of a cell adhesion stimulating protein to a ceramic material.

In a further aspect, the invention pertains to a method for producing a prosthesis. The method includes the harvesting of viable cells from a patient and the adhering of a cell adhesion stimulating protein to a ceramic material. The method further includes the associating of the viable cells with the ceramic material by contacting the ceramic material having adhered protein with a cell culture comprising the viable cells.

BRIEF DESCRIPTION OF THE DRAWINGS

FIG. 13 is a display of six micrographs (magnified 40×) of human aortic endothelial cells growing on six gelatin treated mechanical heart valve leaflets.

FIG. 14 is a display of five micrographs (magnified 40×) of human aortic endothelial cells growing on five mechanical heart valve leaflets treated with gelatin and VEGF.

FIG. 15 is a display of six micrographs (magnified 40×) of human aortic endothelial cells growing on six mechanical heart valve leaflets treated with fibronectin and vitronectin proteins.

DETAILED DESCRIPTION OF THE ILLUSTRATIVE EMBODIMENTS

Figure 1:
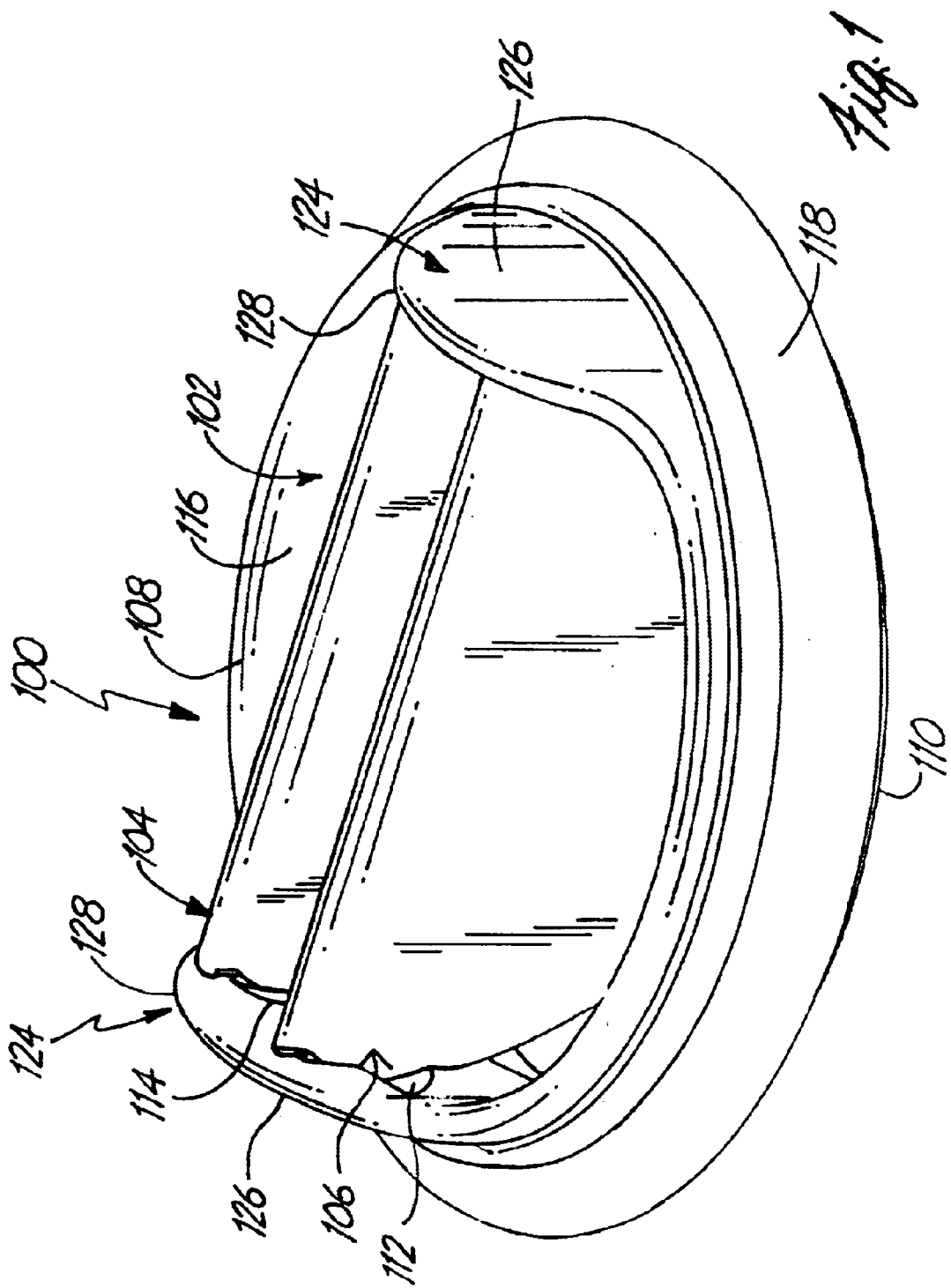
FIG. 1 is a perspective view of a bi-leaflet mechanical heart valve prosthesis.

At least a portion of the surface of a biocompatible ceramic or carbon material can be associated with a cell adhesion stimulating protein, such that viable endothelial cells colonize the ceramic or carbon material. For convenience, carbon based solids, such as pyrolytic carbon, are considered within the ceramic material class herein, except as otherwise noted. The cell adhesion stimulating protein can be a structural protein, a polypeptide growth factor, a fragment or modified form thereof, or a combination thereof.

The ceramic material incorporated into a medical article generally would not undergo cellularization by endothelial cells without the presence of the protein, or the ceramic material would cellularize much more slowly. The presence of an endothelial cell layer coating surfaces of a prosthesis, such as a prosthetic valve, can impart improved durability to a bioprosthetic heart valve and added thromboresistance to a mechanical heart valve. A mechanical heart valve with increased thromboresistance is a major improvement in prosthetic heart valve technology.

Thus, the ceramic material is transformed to be able to support cell proliferation by the directed association of structural proteins and/or polypeptide growth factors with the ceramic-material. The ceramic material can form all or just a portion of a medical device, such as a prosthesis. In particular, the ceramic material can form a coating over a substrate or preform. In addition, the ceramic material can be combined with other materials in forming the medical device or a component thereof, such that portions of the medical device do not have a ceramic material at the surface.

The biocompatible ceramic materials described herein are suitable for the preparation of a variety of medical articles, such as prostheses. Prostheses, i.e., prosthetic articles, are used to repair or replace damaged or diseased organs, tissues and other structures in humans and animals. Prostheses generally must be biocompatible since they are typically implanted for extended periods of time in contact with bodily fluids and tissues of a patient. Preferred prostheses include prostheses used in the cardiovascular system and the vascular system. Relevant prostheses generally incorporate a biocompatible material which is intended to contact the patient's bodily fluids and/or tissues. Bodily fluids include, for example, blood, plasma, serum, interstitial fluids, saliva and urine. The patient can be an animal, especially a mammal, and preferably is a human.

Through the association of cell adhesion stimulating proteins, ceramic materials can be modified to support colonization by viable cells. It is particularly advantageous to associate both a structural protein and a growth factor with the ceramic material. The growth factor can encourage colonization of viable cells while the structural proteins help to anchor the viable cells to the surface of the ceramic material. The character, in particular the surface properties, of these ceramic materials can be significantly altered through the attachment of viable cells. The colonization by viable cells can be performed either in vivo or in vitro.

Suitable structural proteins include, for example, protein components of the extracellular matrix. Preferred polypeptide growth factors include vascular endothelial growth factor (VEGF) and related compounds. Following modification of the ceramic material with VEGF, the VEGF can stimulate endothelial cell chemotaxis and proliferation. VEGF modification is particularly suitable for the production of prostheses that naturally have an endothelial or epithelial cell lining, such as vascular components, cardiovascular structures, portions of the lymphatic system, uterine lining or retinal tissue.

The cell adhesion stimulating protein can be associated with the ceramic materials in a variety of ways. For example, the ceramic materials can be combined with a solution of the cell adhesion stimulating protein such that the cell adhesion stimulating protein becomes joined with the prosthetic ceramic material by direct attachment, involving adsorption, absorption or physical association. Alternatively, the cell adhesion stimulating protein can be associated with the prosthetic ceramic material using an adhesive. In addition, the cell adhesion stimulating protein can be joined with the prosthetic ceramic material using chemical bonding.

Preferred biocompatible materials are rigid structures formed from a material in the ceramics class, such as specifically a ceramic, a ceramic coating, a carbon material or a carbon coating. However, flexible structures with a ceramic or carbon coating can be formed. In particular, it has been found that a diamond-like carbon coating can be applied over a flexible polymer to produce a flexible structure that can be flexed repeatedly without damaging the diamond-like carbon coating. The flexible diamond-like carbon coated polymers are suitable for the formation of flexible leaflets for heart valve prostheses. Diamond-like carbon coated flexible polymers are described further in copending and commonly assigned U.S. patent application Ser. No. 09/437,167, entitled "Medical Device With Diamond-Like Carbon Coating on a Polymer Substrate," incorporated herein by reference.

The ceramic material with an associated cell adhesion stimulating protein forms a prosthesis or a portion of a prosthesis. Cells can be associated with the ceramic material in vitro prior to implantation or in vivo following implantation into the patient. In particular, the cell adhesion stimulating protein can effectively induce the colonization and/or proliferation of viable cells, such as endothelial cells, on the ceramic material in vitro or in vivo such that the ceramic surface becomes populated with viable cells. The presence of the viable cells on the surface of the ceramic material modifies the surface properties of the ceramic material. These viable cells perform functions associated with native endothelial cells including reduction or inhibition of thrombosis.

For in vivo growth, the ceramic material with one or more associated cell adhesion stimulating proteins, preferably both a structural protein and a growth factor, can be implanted into a patient. Once implanted in the patient, viable cells from the patient, such as endothelial cells, become attached to the prosthesis due to the presence of the cell adhesion stimulating proteins. Alternatively, viable cells can be associated with the prosthesis in a cell culture system. In vitro colonization is demonstrated in the Examples below.

A. Medical Articles

Medical articles can include a biocompatible material, at least as a component, that is suitable as a location for cellular attachment. Generally, these medical articles are designed for implantation into a patient for extended periods of time. Suitable medical articles include, for example, pacemakers, electrical leads such as pacing leads, defibrillators, artificial organs such as artificial hearts, ventricular assist devices, anatomical reconstruction prostheses, heart valve prostheses, tissue patches such as pericardial patches, surgical patches, coronary stents, vascular grafts and conduits, vascular and structural stents, vascular and cardiovascular shunts, annuloplasty rings, stents, staples, valved grafts, orthopedic spinal implants, orthopedic pins, pledgets, suture, permanently in-dwelling percutaneous devices, intrauterine devices (IUDs), urinary stents, maxial facial reconstruction plating, dental implants, clips, sternal wires, bone prosthesis, and combinations thereof. Biomedical devices that are designed to dwell for extended periods of time within a patient are also suitable to include ceramic materials with associated growth factors. These devices include, for example, Hickman catheters.

The biocompatible materials include materials in the ceramics class, which include carbon materials herein. Suitable ceramics include, for example, hydroxyapatite, alumina, zirconia, titanium nitride and boron nitride. Suitable carbon materials and carbon coatings include, for example, pyrolytic carbon, glassy carbon, graphite, amorphous carbon, carbon nitride and diamond-like carbon. A ceramic coating or carbon coating can be deposited on a substrate or preform that can tolerate the deposition conditions.

Pyrolytic carbon is a carbon coating material that is mainly graphitic in nature. If the carbon is ordered such that the material is anisotropic, it is referred to as pyrolytic graphite. Methods for the deposition of pyrolytic carbon include, without limitation, physical vapor deposition, chemical vapor deposition, plasma assisted chemical vapor deposition and fluidized bed chemical vapor deposition. Substrates (preforms) used for chemical vapor deposition generally must be heat resistant.

For deposition using a fluidized bed reactor, the substrate is placed within a bed of particles, such as zirconia beads, that are fluidized by the flow of reactant gases. Pyrolytic carbon can be deposited within a fluidized bed reactor using hydrocarbon gases as reactants. The fluidized bed reactor preferably is set at a temperature selected in part based upon the particular reactant gases used and is typically at a temperature from about 1000° C. to about 2500° C. and more preferably from about 1200° C. to about 1800° C.

Pyrolytic carbon coatings with a broad range of coating thicknesses are readily achieved. A pyrolytic carbon coating deposited by physical vapor deposition generally has an average thickness from about 0.1 microns to about 10 microns.

Preferred deposition approaches are based on chemical vapor deposition. Pyrolytic carbon coating deposited by chemical vapor deposition generally have thickness of about 10 microns to about 1000 microns and preferably from about 70 microns to about 500 microns. The pyrolytic carbon coating generally has an average density from about 1.5 grams/cm$^3$ to about 2.4 grams/cm$^{3.}$ The pyrolytic carbon coating preferably is strongly adhered to the underlying substrate (preform) such that the carbon coating will not separate over time from the substrate (preform). However, in some embodiments, such as the production of orifice ring components, the underlying substrate (preform) is removed, for example, by machining, to leave the deposited carbon material. Suitable substrate (preform) materials include refractory metals, silicon carbide, ceramics, such as mullite ($Al_6Si_2O_{13}$) or zirconia (ZrO), and graphites.

The prostheses can include additional components, such as tissue, polymeric material and metal. Polymeric materials can be fabricated from synthetic polymers as well as purified biological polymers. Appropriate synthetic materials may include hydrogels and other synthetic materials that cannot withstand severe dehydration. Construction of the prosthesis can be completed following deposition of appropriate coatings and the like since some of the components of the final prosthesis may not be able to survive the conditions used for processing the ceramic or carbon coated material. For example, some materials degrade if subjected to high temperatures or vacuum conditions.

Appropriate tissue materials include allograft or xenograft tissue. The tissue can be crosslinked, i.e., fixed tissue, or uncrosslinked tissue. Glutaraldehyde or formaldehyde typically is used for fixation, although other fixatives can be used, such as epoxides and other difunctional aldehydes.

Appropriate synthetic polymers include without limitation polyamides (e.g., nylon), polyesters, polystyrenes, polyacrylates, vinyl polymers (e.g., polyethylene, polytetrafluoroethylene, polypropylene and polyvinyl chloride), polycarbonates, polyurethanes, polydimethyl siloxanes, cellulose acetates, polymethyl methacrylates, ethylene vinyl acetates, polysulfones, nitrocelluloses and similar copolymers. Bioresorbable polymers can also be used such as dextran, hydroxyethyl starch, derivatives of gelatin, polyvinylpyrrolidone, polyvinyl alcohol, poly[N-(2-hydroxypropyl)methacrylamide], poly(hydroxy acids), poly (epsilon-caprolactone), polylactic acid, polyglycolic acid, poly(dimethyl glycolic acid), poly(hydroxy buterate), and similar copolymers. Some of these synthetic polymeric materials can be formed into fibers and woven or knitted into a mesh to form a matrix or substrate. Alternatively, the synthetic polymer materials can be molded or cast into appropriate forms.

Biological polymers can be naturally occurring or produced in vitro by, for example, fermentation and the like. Purified biological polymers can be appropriately formed into a material by techniques such as weaving, knitting, casting, molding, extrusion, cellular alignment and magnetic alignment. For a description of magnetic alignments see, for example, R. T. Tranquillo et al., Biomaterials 17:349–357 (1996), incorporated herein by reference. Suitable biological polymers include, without limitation, collagen, elastin, silk, keratin, gelatin, polyamino acids, cat gut sutures, polysaccharides (e.g., cellulose and starch) and copolymers thereof.

Prostheses of particular interest include mechanical heart valve prostheses. A bi-leaflet mechanical heart valve prosthesis 100 is shown in FIG. 1. Heart valve prosthesis 100 includes as components an orifice ring 102 which retains two occluders or leaflets 104, 106. Orifice ring 102 has an upstream surface 108 and a downstream surface 110. Occluders 104, 106 rotate at hinges 112, 114 and two additional hinges symmetrically and oppositely positioned on the inner surface 116 of orifice ring 102. Inner surface 116 of orifice ring 102 forms a flow path through the valve that can be opened or closed through the pivoting of occluders 104, 106. A sewing cuff 118 is placed around orifice ring 102 to facilitate attachment to the patient's tissue during implantation.

Orifice ring 102 and occluders 104, 106 can be formed from rigid elements, such as rigid preforms fabricated from graphite and then coated with pyrolytic carbon. In one embodiment, the preform for orifice ring 102 lumen includes a plug of graphite with inverse features arrayed about its circumference. After coating with pyrolytic carbon, the plug is removed, for example, by abrasive machining leaving the free-standing orifice ring with its luminal features. The completed element for the heart valve component can be associated with one or more cell adhesion stimulating proteins. In one embodiment, upstream surface 108 and downstream surface 110 of orifice ring 102 are associated with the cell adhesion stimulating proteins. In other embodiments, all or a portion of occluders 104, 106 have surfaces associated with cell adhesion stimulating protein.

Generally, the entire medical device or just portions thereof can have associated cell adhesion stimulating proteins. In the embodiment shown in FIG. 1, an orifice ring 102 has a pivot guard structure 124, which projects upstream of the plane of orifice ring 102. In a preferred embodiment, outside circumference 126 and upstream surface 128 of pivot guards 124 are associated with one or more cell adhesion stimulating proteins. In addition, in one embodiment, sewing cuff 118 is formed from a fabric with a ceramic coating, such as pyrolytic carbon, associated with one or more cell adhesion stimulating proteins.

B. Cell Adhesion Stimulating Proteins

Cell adhesion stimulating proteins include, for example, structural proteins, growth factors and combinations thereof. Structural proteins are a class of proteins that primarily provide structural support in contrast with enzymes and transport proteins. Growth factors are proteins that stimulate cell proliferation. In preferred embodiments, a ceramic material is associated with a structural protein and a growth factor, each associated with at least a portion of the surface of the ceramic material. Preferred growth factors include, for example, vascular endothelial growth factor.

As used herein, protein is intended to be broadly interpreted as one or more polypeptide units with or without additional covalently or non-covalently attached components, such as saccharides, lipids, or nucleic acids. Suitable structural proteins include, for example, extracellular matrix protein components. The extracellular matrix includes structural proteins, secreted by cells, which hold the cells together as a cohesive unit. Structural proteins include, for example, collagen, fibronectin, vitronectin and laminin. Gelatin is a heterologous mixture of water soluble proteins derived from collagen by hydrolysis and is also considered a structural protein. Extracellular matrix proteins also include matricellular proteins, such as osteopontin and SPARC (secreted protein acidic and rich in cysteine), that influence cell function. Extracellular matrix proteins can be used directly from extracellular matrix material without purification of the individual proteins. Extracellular matrix material is commercially available, for example, from Sigma Chemical, St. Louis, Mo.

Vascular endothelial growth factor (VEGF) refers to a family of polypeptides that have been found to preferentially stimulate growth of vascular endothelial cells in preference to other cells, such as smooth muscle cells. Alternatively, other less selective growth factors, such as fibroblast growth factor (FGF), may also be used to stimulate endothelial cell proliferation. Several forms of VEGF have been identified. VEGF polypeptides generally have sequence homology with platelet-derived growth factor (PDGF), which can alter the migration and proliferation of a variety of cell types. VEGF occasionally has been referred to as vascular permeability factor.

The originally identified form of VEGF has an apparent molecular weight of about 45 to 46 kilodaltons (kDa). This form is a homodimer, with each subunit having a molecular weight of about 23 kDa. The cDNA sequences encoding the human polypeptide (165-amino acids, $hVEGF_{165}$) and the corresponding bovine polypeptide (164-amino acids, $bVEGF_{164}$) have been determined. In addition, variants of the polypeptides with 121-amino acids for the human version ($hVEGF_{121}$) and 120-amino acids for the bovine version ($bVEGF_{120}$) also have been identified. For the corresponding amino acid sequences, see U.S. Pat. No. 5,194,596, to Tischer et al., incorporated herein by reference. Other insoluble variants with 189 and 206-amino acids, respectively, have been identified. See, for example, E. Tischer et al., "The human gene for vascular endothelial growth factor. Multiple protein forms are encoded through alternative exon splicing," J. Biol. Chem. 266:11947–11954 (1991) and K. A. Houck et al., "The vascular endothelial growth factor family: identification of a fourth molecular species and characterization of alternative splicing of RNA," Molec. Endocrinology 5:1806–1814 (1991), both incorporated herein by reference.

Another form of VEGF, called VEGF II, is a heterodimer. As isolated from rat glioma cells, the first subunit has 190-amino acids while the second subunit has a 135-amino acid form and a 115-amino acid form. VEGF II is described in EP 0 476 983A, incorporated herein by reference.

A single polypeptide human VEGF, unnamed, also has been identified. This polypeptide has a molecular weight of roughly 80 kDa. The corresponding cDNA was isolated and a 728-amino acid sequence was determined from the cDNA sequence. Details of the protein are provided in EP 0 550 296A, incorporated herein by reference.

Still another human growth factor, VEGF2, has been identified from early stage human embryo osteoclastomas, adult heart and several breast cancer lines. VEGF2 has 350 amino acids, of which about 24 amino acids represent a leader sequence. The sequence for VEGF2 is disclosed in WO 95/24473, incorporated herein by reference.

Recently, VEGF-B, another variant of VEGF, has been identified. VEGF-B appears to be associated with heart and skeletal muscles. Full sequences for mouse and human VEGF-B are presented in U.S. Pat. No. 5,607,918, to Eriksson et al., incorporated herein by reference.

In addition to VEGF variants that are expressed in mammalian cells under normal physiological conditions, viral proteins such as the Tat protein from human immunodeficiency virus (HIV)-1 share sequence homology with VEGF and bind to native VEGF receptors. These properties are described in Albini et al., "The angiogenesis induced by HIV-1 Tat protein is mediated by the Flk-1/KDR receptor on vascular endothelial cells," Nature Medicine 2(12): 1371–1375 (1996) and Mitola et al., "Tat-human immunodeficiency virus-1 induces human monocyte chemotaxis by activation of vascular endothelial growth factor receptor-1," Blood 90 (4):1365–1372 (1997), both of which are incorporated herein by reference. Through an interaction with VEGF receptors, a Tat protein stimulates endothelial cell chemotaxis and proliferation. Thus, for the purposes of this application, the Tat protein and other similar viral proteins that bind VEGF receptors are considered VEGF growth factors.

As described above, a variety of VEGF polypeptides have been identified. Many of these are associated with particular tissues. At least some of the polypeptides have variations based on alternative message splicing, such as $hVEGF_{165}$ and $hVEGF_{121}$. As used in the other sections of this application, "VEGF" refers, without limitation, to all previously identified VEGF polypeptides, such as those described in this section, as well as any future identified VEGF polypeptides that selectively promote the chemotaxis or proliferation of endothelial cells. "VEGF" also refers to polypeptide fragments that maintain their ability to selectively promote the chemotaxis or proliferation of endothelial cells. As noted above, for example, human $VEGF_{121}$ is a naturally occurring fragment of human $VEGF_{165}$. Recombinant human $VEGF_{165}$, human $VEGF_{121}$, and mouse VEGF are available from R&D Systems of Minneapolis, Minn. Similarly, "VEGF" referred to herein includes VEGF proteins modified by chemical additions to the protein molecule by covalent or noncovalent binding.

Using standard molecular biology techniques (see, for example, Sambrook, Fritsch and Maniatis, "Molecular Cloning: A Laboratory Manual," 2nd edition, Cold Spring Harbor Press, (1989)), it is possible to make recombinant modified forms of natural VEGF polypeptides. These straightforward modifications include addition of amino acids on the N-terminus, the C-terminus or both. Also, modifications can be made by substituting amino acids along the polypeptide chain. Some modifications may destroy activity of the protein. It is straightforward to eliminate inactivating modifications by testing for activity in cell culture systems. Active forms of these modified polypeptides are within the general definition of "VEGF."

C. Joining of the Cell Adhesion Stimulating Protein with a Ceramic Material

The joining of one or more cell adhesion stimulating proteins with a ceramic material can involve direct attachment, application of a coating including an adhesive, or chemical bonding. A cell adhesion stimulating protein may be joined with only a portion of a ceramic material or over the entire surface of the ceramic material. The proteins generally are located at or near the surface of the ceramic material, although some of the protein can penetrate into the ceramic material. If the cell adhesion stimulating protein is bound to a portion of the ceramic material, cells may still associate with other portions of the ceramic material not bound with the cell adhesion stimulating protein as a result of the cell adhesion stimulating protein being present on part of the ceramic material. A plurality of cell adhesion stimulating proteins can be used, which are located at the same portion(s) of the medical device or at different locations.

As noted above, cell adhesion stimulating proteins include, for example, structural proteins and growth factors. While either structural proteins or growth factors can stimulate cell association with the ceramic material, a combination of a structural protein and a growth factor can result in enhanced cell association. Generally, if multiple cell adhesion stimulating proteins are associated with the ceramic material, each protein can be associated with the ceramic material prior to associating subsequent protein(s) with the ceramic material, i.e., the proteins are associated sequentially with the ceramic material. Alternatively, a plurality of different proteins can be associated with the ceramic material simultaneously. The in vitro examination of effectiveness at stimulating cell attraction and proliferation described in the Examples below can be used to evaluate the effectiveness of a particular association approach.

Direct attachment entails combining a surface portion of the ceramic material with a solution of the cell adhesion stimulating protein. In particular, it has been discovered that a cell adhesion stimulating protein can associate with a ceramic or carbon coated material such that the cell adhesion stimulating protein does not readily wash off. In particular, the ceramic material can be rinsed periodically and the cell adhesion stimulating protein remains associated with the ceramic material.

A chemical crosslinking agent that crosslinks protein molecules can be used to enhance the direct association of the protein with the ceramic material. Suitable protein crosslinking agents include, for example, glutaraldehyde, formaldehyde, epoxides and other difunctional aldehydes. The crosslinking can be performed for at least about 5 minutes and generally is performed for about 15 minutes to about 24 hours or longer. In particular, the crosslinking of cell adhesion stimulating protein can be performed preferably for less than about 1 hour and, more preferably, for between about 15 minutes and about 30 minutes.

If desired, a size exclusion membrane, such as dialysis tubing, can be used during the simultaneous incubation of cell adhesion stimulating protein and crosslinking agent. For example, dialysis tubing with a 10,000 molecular weight cutoff can be used to contain the ceramic material and the cell adhesion stimulating protein solution in a relatively small volume. The tubing with the ceramic material and the protein can be immersed in a dilute solution of crosslinking agent. The crosslinking agent can permeate the dialysis tubing, but the protein solution remains inside the tubing due to its larger molecular size. This procedure allows for the use of a small volume of protein and a relatively larger volume of crosslinking solution.

For direct attachment of cell adhesion stimulating protein to a ceramic material, the ceramic material or a portion thereof is combined with a solution of cell adhesion stimulating protein at a concentration generally from about 1 ng/ml to about 1 μg/ml and preferably from about 25 ng/ml to about 250 ng/ml. During incubation with the cell adhesion stimulating protein, the solution preferably is cooled, for example, to about 4° C. The ceramic material preferably remains in the cell adhesion stimulating protein solution at about 4° C for about 30 minutes and up to about 24 hours or more. The cell adhesion stimulating protein solution preferably is buffered at a pH ranging from about 5.5 to about 8.5, preferably from about 6.0 to about 8.0, and more preferably ranging from about 6.3 to about 7.4. Suitable buffers can be based on, for example, the following ions or compounds: phosphate, borate, bicarbonate, carbonate, cacodylate, citrate, and other organic buffers such as tris (hydroxymethyl)aminomethane (TRIS), N-(2-hydroxyethyl)piperazine-N'-(2-ethanesulfonic acid) (HEPES), and morpholine propanesulphonic acid (MOPS).

Alternatively, cell adhesion stimulating protein can be associated with the ceramic material through the use of a binder or adhesive. The cell adhesion stimulating protein and the adhesive form a coating on the ceramic material. Suitable adhesives can include natural polymers, synthetic polymers or both. Suitable synthetic adhesives can include urethane-based polymers, such as polymers formed from p-phenylene diisocyanates and polyols. Preferred adhesives include, for example, biologic glues such as fibrin glue, and other protein based glues. Fibrin glue can be formed from the polymerization of fibrinogen and thrombin. Suitable fibrin glues are available from, for example, Immuno AG, Austria and Zymogenetics, Seattle, Wash. Fibrin glues containing albumin are described in U.S. Pat. No. 4,414,976 to Schwarz et al., incorporated herein by reference.

To apply the cell adhesion stimulating protein with, for example, a fibrin glue, a small amount of thrombin can be absorbed to the ceramic material. Cell adhesion stimulating protein can be mixed with a solution containing fibrinogen to yield a solution with a cell adhesion stimulating protein concentration preferably ranging from about 1 ng/ml–10 μg/ml. Then, the fibrinogen/cell adhesion stimulating protein mixture can be brushed over the surface of the ceramic material with absorbed thrombin, or the ceramic material with absorbed thrombin can be dipped into the protein mixture solution. The cell adhesion stimulating protein-adhesive coating can be applied to all or just a portion of the ceramic material.

Fibrin glues and similar glues are resorbed slowly by the patient following application. As an alternative to using an adhesive, cell adhesion stimulating protein can be mixed with other resorbable polymers and formed into a coating on a ceramic material. Suitable resorbable polymers include, for example, dextran, hydroxyethyl starch, gelatin, derivatives of gelatin, polyvinylpyrrolidone, polyvinylalcohol, poly[N-(2-hydroxylpropyl)methacrylamide], polyglycols, polyesters, poly(orthoesters), poly(ester amides), and polyanhydrides. Resorbable polyesters include, for example, poly(hydroxy acids) and copolymers thereof, poly(ε-caprolactone), poly(dimethyl glycolic acid), and poly (hydroxy butyrate). Preferred resorbable polymers include, for example, D,L-polylactic acid, L-polylactic acid, poly (glycolic acid), and copolymers of L-lactic acid, D-lactic acid and glycolic acid. Furthermore, the cell adhesion stimulating protein can be stored in interstices of a polymer matrix that is coated onto or other wise associated with the ceramic material. The polymer matrix can be resorbable to release the cell adhesion stimulating protein or have appropriate porosity such that the cell adhesion stimulating protein can gradually diffuse out to the surface of the ceramic material.

For embodiments in which the cell adhesion stimulating protein includes a growth factor, the various approaches for applying the protein to a ceramic material based on natural or synthetic bioresorbable polymers have the advantage of establishing a concentration gradient of growth factor. As the growth factor is released near the surface of the biocompatible material, the growth factor can act as a chemotactic agent signaling cells to migrate toward a higher concentration of growth factor. Also, a more precise dose can be delivered over a limited period of time.

Regardless of the nature of the association interaction, the bound cell adhesion stimulating protein generally is in equilibrium with unbound protein. As a result, the protein may eventually be lost from the prosthesis to the surrounding solution. For some applications, it may be sufficient for the protein to be bound for a relatively short period of time, such as hours or days, if sufficient viable endothelial cells proliferate on the ceramic material during the relevant time. In other circumstances, it may be desirable for longer term binding of the cell adhesion stimulating protein to the ceramic material, such as months or years. The nature of the association of the cell adhesion stimulating protein with the ceramic material can be selected accordingly.

D. Other Modifiers

It may be desirable to associate other molecules with a ceramic material, in addition to cell adhesion stimulating proteins, to improve the colonization and/or proliferation of cells on the ceramic material's surface in a medical article. For example, matricellular proteins, such as osteopontin and secreted protein acidic and rich in cysteine (SPARC) may modulate endothelial cells to make them more or less responsive to growth factors. In addition, matrix components, such as glycosaminoglycans and proteoglycans can impart added antithrombotic potential that may augment thromboresistance particularly during the period immediately following implant before a complete monolayer of endothelial cells has been achieved.

E. In vitro Attachment of Endothelial Cells

Growth of viable endothelial cells on a prosthesis prior to implantation into a patient can be promoted in vitro by joining cell adhesion stimulating proteins, such as VEGF, with a ceramic material. In order to reduce the possibility of immune system rejection, endothelial cells used for in vitro endothelialization preferably are autologous cells, i.e., cells from the recipient patient. Suitable cells could be harvested from, for example, adipose tissue of the patient.

The harvesting process can involve liposuction followed by collagenase digestion and purification of microvascular endothelial cells. Suitable processes for endothelial cell harvesting are described further in S. K. Williams, "Endothelial Cell Transplantation," Cell Transplantation 4:401–410 (1995), incorporated herein by reference and in U.S. Pat. No. 4,883,755 to Carabasi et al., entitled "Method of Reendothelializing Vascular Linings, U.S. Pat. No. 5,372,945 to Alchas et al., entitled "Device and Method for Collecting and Processing Fat Tissue and Procuring Microvessel Endothelial Cells to Endothelial Cell Product," and U.S. Pat. No. 5,628,781 to Williams et al., entitled "Implant Materials, Methods of Treating the Surface of Implants With Microvascular Endothelial Cells, and the Treated Implants Themselves," all three patents incorporated herein by reference. Purified endothelial cells can be suspended in an appropriate growth media such as M199E (e.g., Sigma Cell Culture, St. Louis, Mo.) with the addition of autologous serum.

Medical devices or components thereof with bound VEGF can be incubated with endothelial cells for a period of hours to days to allow for endothelial cell seeding. Cell seeding provides random attachment of endothelial cells that can proliferate to coat the surface of the prosthetic ceramic material either before or after implantation into the patient. Alternatively, the prosthetic ceramic material can be incubated under a pressure gradient for a period of minutes to promote cell sodding. A suitable method for cell sodding can be adapted from a procedure described for vascular grafts in the S. K. Williams article, supra. Cell sodding can produce a monolayer of cells on the surface of the prosthetic tissue. If either attachment or migration of endothelial cells is performed under conditions involving physiological shear stress, then the endothelial cells colonizing the surface of the ceramic material may express appropriate adhesion proteins that allow the cells to adhere more tenaciously following implantation.

F. In vivo Cell Colonization of the Ceramic Material

In other preferred embodiments, the ceramic materials are intended to be colonized in vivo following implantation of the ceramic material. This approach avoids the need for harvesting cells from the patient and growing the cells in a culture system. On the other hand, ceramic materials in vascular environments are likely to experience shear stresses due to fluid flow. These shear stresses place further demands on the effectiveness of the cell adhesion stimulating proteins.

For in vivo cell colonization, it is especially preferred to use a combination of structural proteins and growth factors. The structural proteins provide a better surface for cell adhesion, such that they can adhere to the ceramic material without being carried away by the fluid flow, and the growth factors promote more rapid cell proliferation.

The implantation of heart valve prostheses is of particular interest. In these embodiments, the orifice ring and/or one or more occluders can include a surface with associated cell adhesion stimulating protein. The potential advantages of having a layer of endothelial cells on the surface of the orifice ring and/or occluder are significant. For example, the likelihood of thrombosis may be reduced, thereby decreasing the requirements for anticoagulants.

In vivo shear stresses may be greater on a rigid or relatively rigid heart valve prosthesis, as compared to a native valve. These stresses may be particularly high on certain portions of the orifice ring or occluder. In some cases, these stresses may be too high to allow for endothelial cell adhesion and/or survival or the shear stress may activate any endothelial cells present such that those cells are no longer anti-thrombotic. However, significant thromboresistance may result from endothelial cell coverage of only portions of the prosthesis. For example, increased thromboresistance can be achieved by obtaining endothelial coverage of surfaces exposed to low shear and/or stagnant flow, such as leading edges of leaflets, and/or orifice rings and/or orifice ring pivot guards. Thus, it may be possible to coat only those portions of the prosthesis where shear stress is within physiological limits and those areas most prone to thrombosis.

In addition to providing thromboresistance, endothelial cell coverage may provide a barrier against infection, such as infection of the sewing cuff resulting in prosthetic valve endocarditis. Also in the case of polymer valves, an endothelial cell monolayer may help to prevent calcification.

G. Storage, Packaging, Distribution and Use

Following binding of cell adhesion stimulating protein to a ceramic material, the ceramic material, which generally forms at least part of a component of a prosthesis, can be stored. Preferred storage techniques minimize the risk of microbial contamination. For example, the modified ceramic material can be stored in a sealed container with sterile buffer and/or saline solution. The storage approach should take into account the storage requirements of the different components of the medical device. For example, a mechanical heart valve prosthesis with pyrolytic carbon coated graphite components having associated VEGF can be stored in an antiseptic aqueous solution.

In a sealed container, the modified ceramic material is not subjected to a continuous supply of fluids. Nevertheless, consideration should be given to possible loss of cell adhesion stimulating protein or protein activity from the ceramic material during storage. If excessive loss is a possibility, the storage time can be limited appropriately to keep the loss to an acceptable level.

For distribution, the prostheses generally are placed in sealed and sterile containers. The containers can be dated such that the date reflects the maximum advisable storage time accounting for possible loss or degradation of protein activity. The containers are distributed to health care professionals for surgical implantation of the prostheses. In vitro association of cells with a protein modified prosthesis preferably is performed at hospitals where the patient's cells can be removed for use in a cell culture system.

As an alternative to the above storage and distribution approach, the modification of the ceramic material with cell adhesion stimulating protein can be performed at a hospital or other site separate from the manufacturing site, if desired. Under these circumstances, the prosthesis, with ceramic material suitable for modification, is distributed and association of cell adhesion stimulating protein is performed at a later time. Once the prosthesis is modified with protein, it can be implanted, stored for a reasonable period of time (up to one month or more) or introduced into a cell culture system to affiliate cells, preferably autologous cells, with the protein modified prosthesis.

In certain specific preferred embodiments, the prepared prosthesis, a protein solution and a binding solution (if desired) are shipped in separate containers, either as a kit to be used together or as separate articles for use in desired combinations. In particular, the solution of cell adhesion stimulating protein can be shipped with instructions for modifying a ceramic material with the protein. The prosthesis and the solutions are combined immediately prior to use. After the prosthesis has been incubated in the solutions for a specified period of time, the prosthesis is removed from the solution, rinsed with a sterile saline solution and implanted into the patient.

Incorporation of VEGF or other proteins into a prosthesis to promote endothelialization of a ceramic material should improve biocompatibility of the ceramic material following implantation. In particular, a quiescent endothelial cell monolayer can serve as a barrier to infection, inflammation, and, possibly, calcification. Ultimately, endothelialization can provide for a prosthesis that has thromboresistant surface properties more closely resembling a native, biologically competent tissue.

EXAMPLES

Example 1

Addition of VEGF to Pyrolytic Carbon-Coated Occluders and to Sewing Cuff Fabric

This Example demonstrates the ability of VEGF to associate with a substrate coated with pyrolytic carbon and the ability of VEGF to promote endothelialization of a substrate coated with pyrolytic carbon.

The wells of a six well tissue culture plate were coated with 2% gelatin and seeded with passage 5 human aortic endothelial cells (HAECs) in five mls endothelial growth media (EGM). Cells (lot HAEC 2508) and media were purchased from Clonetics, Inc., San Diego, Calif. Cells were allowed to grow to confluence over a five day period changing media every other day.

Clinical grade mechanical heart valve occluders coated with pyrolytic carbon and both uncoated and Silver-coated (an antimicrobial metal coating) polyester sewing cuff fabric were sterilized by autoclaving at 270° C. for 20 minutes. From this point on, aseptic technique was employed in all procedures to maintain sterility. Fabric was cut into 1 cm square samples.

A glutaraldehyde/HEPES-buffered saline solution (HBSS) was made by combining 50 ml HBSS (Clonetics, Inc.) with 10 $\mu$l 50% by volume glutaraldehyde to achieve a final glutaraldehyde concentration of 0.01%. Ten mls of this glutaraldehyde/HBSS solution was combined with 100 $\mu$l of 10 $\mu$g/ml VEGF (R&D Systems, Minneapolis, Minn.) to achieve a final concentration of 100 ng/ml VEGF.

One pyrolytic carbon-coated occluder, one uncoated polyester fabric sample and one silver-coated polyester fabric sample were immersed in the 10 ml VEGF solution for thirty minutes at room temperature. During this period another pyrolytic carbon-coated occluder and another uncoated polyester fabric sample were incubated in a control solution of 0.01% glutaraldehyde/HBSS containing no VEGF. At the end of the thirty minute incubation period, samples were rinsed three times in 100 ml of sterile 0.9% saline.

The tissue culture plate containing confluent HAECs was removed from the incubator. Then, the center portion of each well was scraped clear of cells using a sterilized rubber policeman. Wells were rinsed with EGM to remove cellular debris. Pyrolytic carbon-coated occluders or fabric samples were placed in the cleared portion of each well. One well was kept clear of samples to use as a control. The following summarizes the samples used:

| | |
|---|---|
| Well 1 | No sample |
| Well 2 | Pyrolytic carbon-coated occluder with NO VEGF |
| Well 3 | Pyrolytic carbon-coated occluder treated with 100 ng/ml VEGF |
| Well 4 | Uncoated polyester sewing cuff fabric with NO VEGF |
| Well 5 | Uncoated polyester sewing cuff fabric with 100 ng/ml VEGF |

| | |
|---|---|
| Well 6 | Silver-coated polyester sewing cuff fabric with 100 ng/ml VEGF |

After addition of the samples to the wells, the wells were rinsed again and covered with fresh EGM media. Then, the tissue culture plate was returned to the incubator for a period of five days. Media was changed every other day.

At the end of five days, the wells were rinsed three times with Dulbecco's phosphate buffered saline (D-PBS from Gibco/BRL, Grand Island, N.Y.), and any cells adhering to the occluders or fabric were fixed in place with 3% formaldehyde. After fixing the cells, samples were rinsed three times with reverse osmosis (RO) purified water and then rinsed once with 0.25 M sucrose. Samples were then covered with a 50 μM solution of a fluorescent, lipophilic probe, dioctadecyl tetramethyl indocarbocyanine perchlorate (DiI) stain from Molecular Probes, Inc., Eugene, Oreg. (catalog no. D-282) in 0.25 M sucrose. DiI is a cell membrane stain. Both samples and solution were kept in the dark from this point on to avoid bleaching of the fluorescent DiI. Samples were stained with DiI for 20 minutes, and then were rinsed four times with RO water. Samples were then covered with enough 0.9% saline to prevent them from drying out. Stained samples were imaged using a reflecting optical microscope with a tetramethylrhodamine isothiocyanate (TRITC) filter and photographed.

Figure 2:
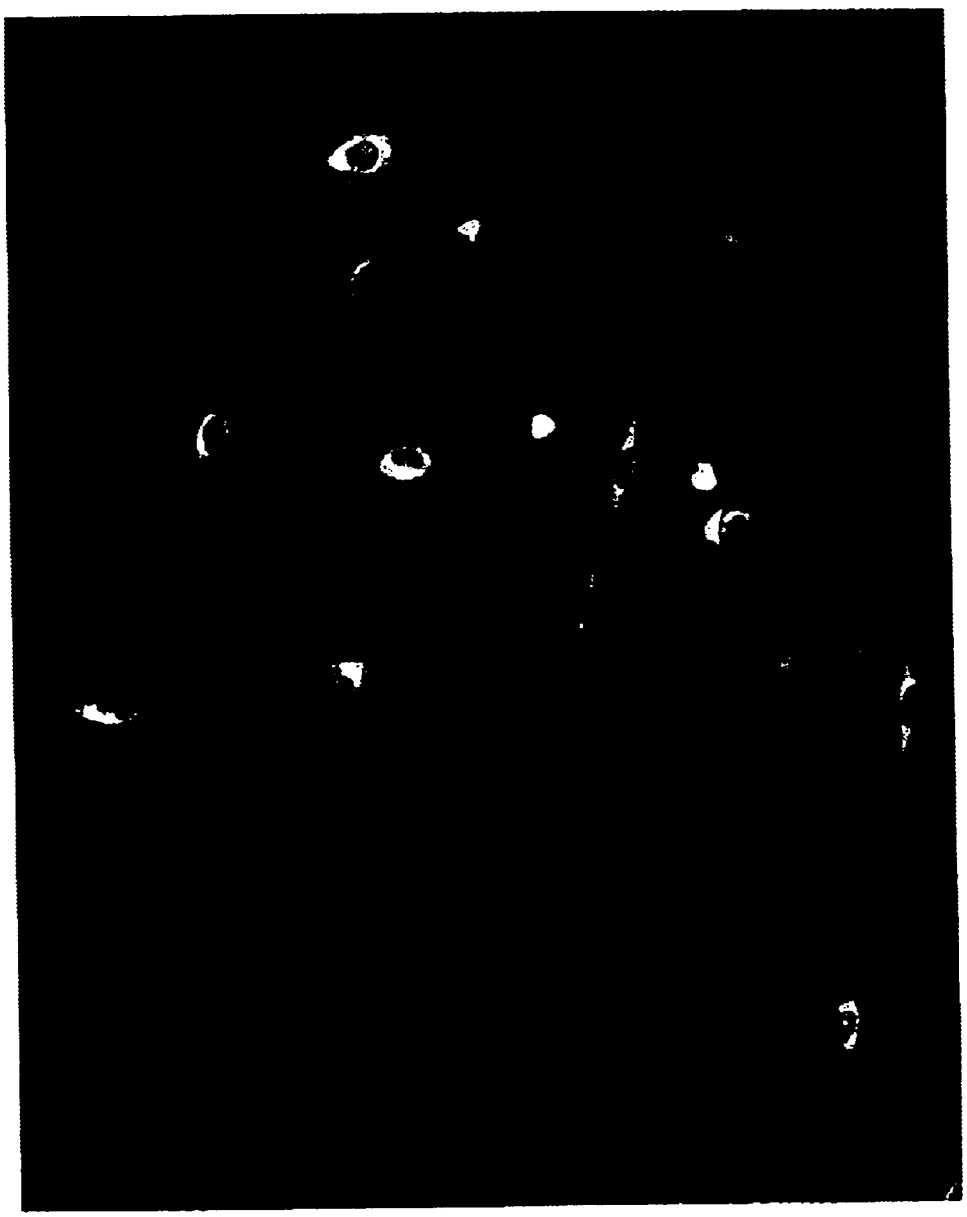
FIG. 2 is a micrograph (magnified 200×) of human aortic endothelial cells growing on a vascular endothelial growth factor (VEGF) treated mechanical heart valve leaflet formed from pyrolytic carbon.

Based on an examination of the stained samples, no cells grew on the untreated pyrolytic carbon coated occluder, although some cellular debris was observed on the pyrolytic carbon. Only background fluorescence was observed with samples lacking cells when examined through the TRITC filter. Samples with VEGF adsorbed to the surface had brightly fluorescent cells attached to the pyrolytic carbon, indicating stimulation of endothelial cell migration toward the pyrolytic carbon and of adherence to the pyrolytic carbon. This can be seen in FIG. 2 for a representative view of the VEGF occluder placed in a section of a well initially clear of endothelial cells. There were no cells on any of the fabric samples. This Example demonstrates that addition of VEGF can promote association of HAECs with a pyrolytic carbon-coated occluder in vitro.

Example 2

Stimulation of Cell Adhesion by Structural Proteins With or Without VEGF

This Example demonstrates that gelatin and extracellular matrix material as well as VEGF are capable of stimulating cell growth in association with a pyrolytic carbon coated material.

Tissue culture inserts were placed in the wells of two six well culture plates. The 30 mm diameter membranes constituting the floor of these inserts was coated with 2% gelatin and seeded with HAECs in EGM media. HAECs were allowed to grow to confluence, as described in Example 1. Clinical grade pyrolytic carbon-coated occluders were autoclaved, also as described in Example 1.

The following solutions were prepared fresh on the day of use. All solutions were made from sterile reagents using aseptic techniques to preserve sterility. A VEGF solution was made by combining 12 ml of HBSS (Clonetics, Inc. San Diego, Calif.) with 2.4 μl 50% by volume glutaraldehyde and 120 μl of 10 μg/ml VEGF (R&D Systems, Minneapolis, Minn.). The final concentration of VEGF was 100 ng/ml. A control solution was made by combining 15 ml of HBSS with 3.0 μl of 50% glutaraldehyde with no VEGF. A 2% by weight gelatin solution was obtained from Sigma Chemicals (St. Louis, Mo.) and warmed to 37° C. before use. A 10 mg/ml extracellular matrix solution (ECM gel—catalog #E-1270, lot #107H4088) derived from Engolbroth Holm-Swarm mouse sarcoma was also obtained from Sigma Chemical and was warmed to room temperature before use.

For incubation, sterilized pyrolytic carbon-coated occluders were placed in individual wells of two new six-well tissue culture plates. Additions were made to each well of both plates as follows:

| | |
|---|---|
| Wells 1 & 2 | No solution |
| Wells 3 & 4 | Two ml of 2% gelatin |
| Wells 5 & 6 | Two ml of ECM gel |

Occluders were allowed to incubate in these wells at room temperature for one hour. At the end of this time, the solution was removed by aspiration and 2 ml of either control or VEGF solution was added to appropriate wells of both plates as follows:

Well 1, 3, 5—control solution

Well 2, 4, 6—VEGF solution

Occluders were allowed to incubate in these solutions for 30 minutes at room temperature. Wells were then rinsed three times with sterile 0.9% saline and covered with 2 ml EGM growth media.

The tissue culture plates containing confluent HAECs grown on tissue culture inserts were removed from the incubator and an eight mm hole was cut in the center of each insert using a biopsy punch. The inserts were transferred to the plates containing the occluders. One insert was placed over the top of each occluder such that the edges of the hole in the center of each insert made contact with the top of the occluder. Wells were rinsed then covered with five ml fresh EGM media and returned to the incubator. Cells were incubated with the occluders for a period of five days with EGM replaced every other day.

At the end of this period, the culture plates were removed from the incubator. Any cells adhering to occluders were analyzed either by staining with DiI (plate 1) or by Live/Dead staining (plate 2). DiI staining was accomplished essentially as described in Example 1. The DiI stained samples were imaged using a tetramethylrhodamine isothiocyanate filter and photographed. Live/Dead staining was used to assess cell viability as well as number.

The Live/Dead assay is a two-color fluorescence cell viability assay that differentiates between live and dead cells using two dyes, calcein AM and ethidium homodimer. The calcein AM stains viable cells due to intracellular esterase activity. Intracellular esterase activity is measured by the enzymatic conversion of the non-fluorescent, cell-permeable calcein AM to the intensely green fluorescent calcein. Cells with intracellular esterase activity fluoresce green, indicating live cells. Ethidium homodimer, which only enters cells through damaged membranes, binds to nucleic acids producing a red fluorescence. Cells with damaged membranes fluoresce red, indicating dead cells.

The Live/Dead assay was performed as follows: Each sample was incubated in one ml of stain containing 10 μM calcein AM and 8 μM ethidium homodimer for 2.5 hours at 37° C. After incubation, samples were rinsed with D-PBS and viewed, at wavelengths 530 nm (calcein) and 600 nm (ethidium homodimer), using a Nikon® Ellipse 600 microscope with epi-fluorescence attachment. Images were processed using Image Pro+® 3.0 software.

Figure 3:
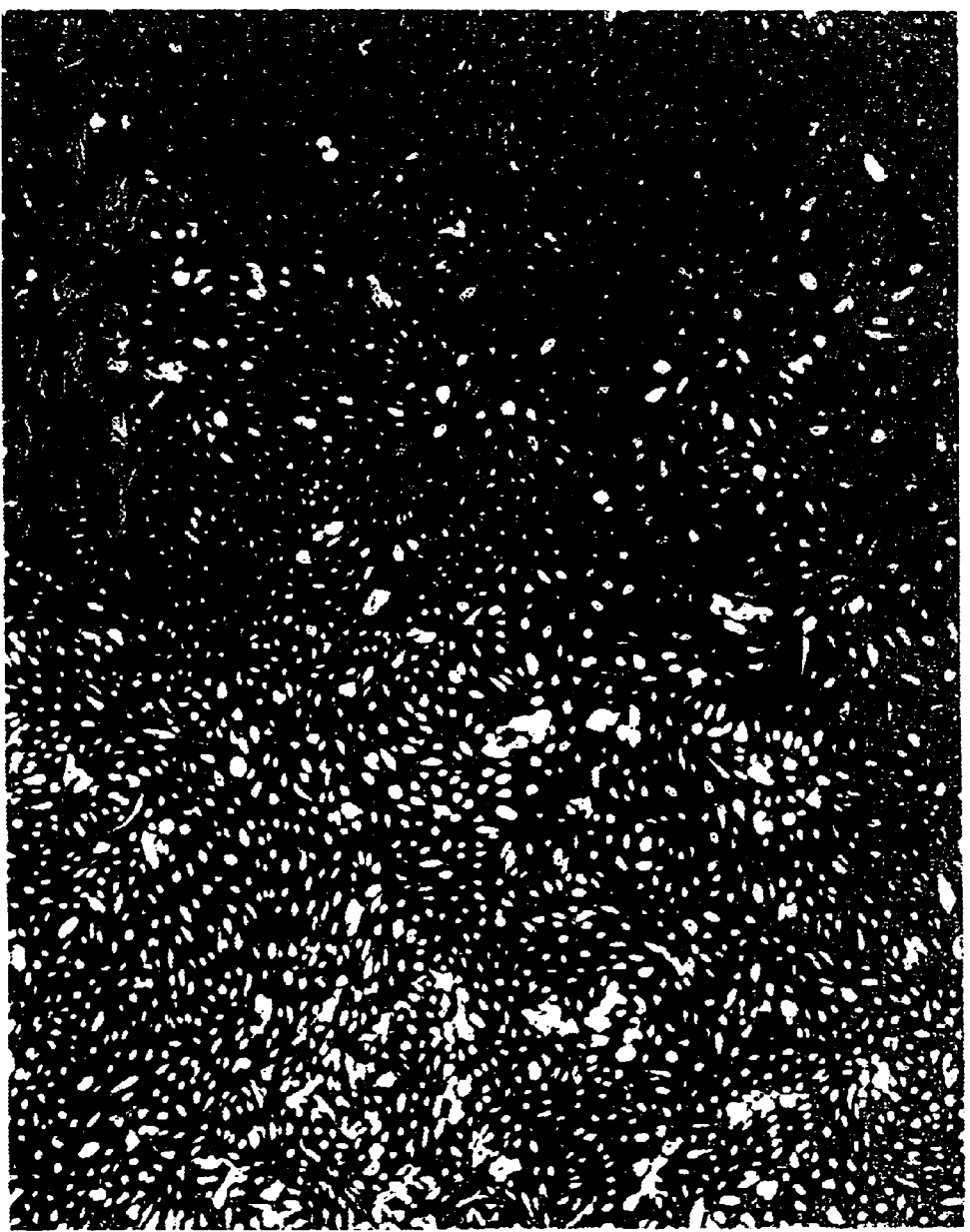
FIG. 3 is a micrograph (magnified 40×) of human aortic endothelial cells growing on a VEGF treated mechanical heart valve leaflet from a different experiment than shown in FIG. 2.
Figure 4:
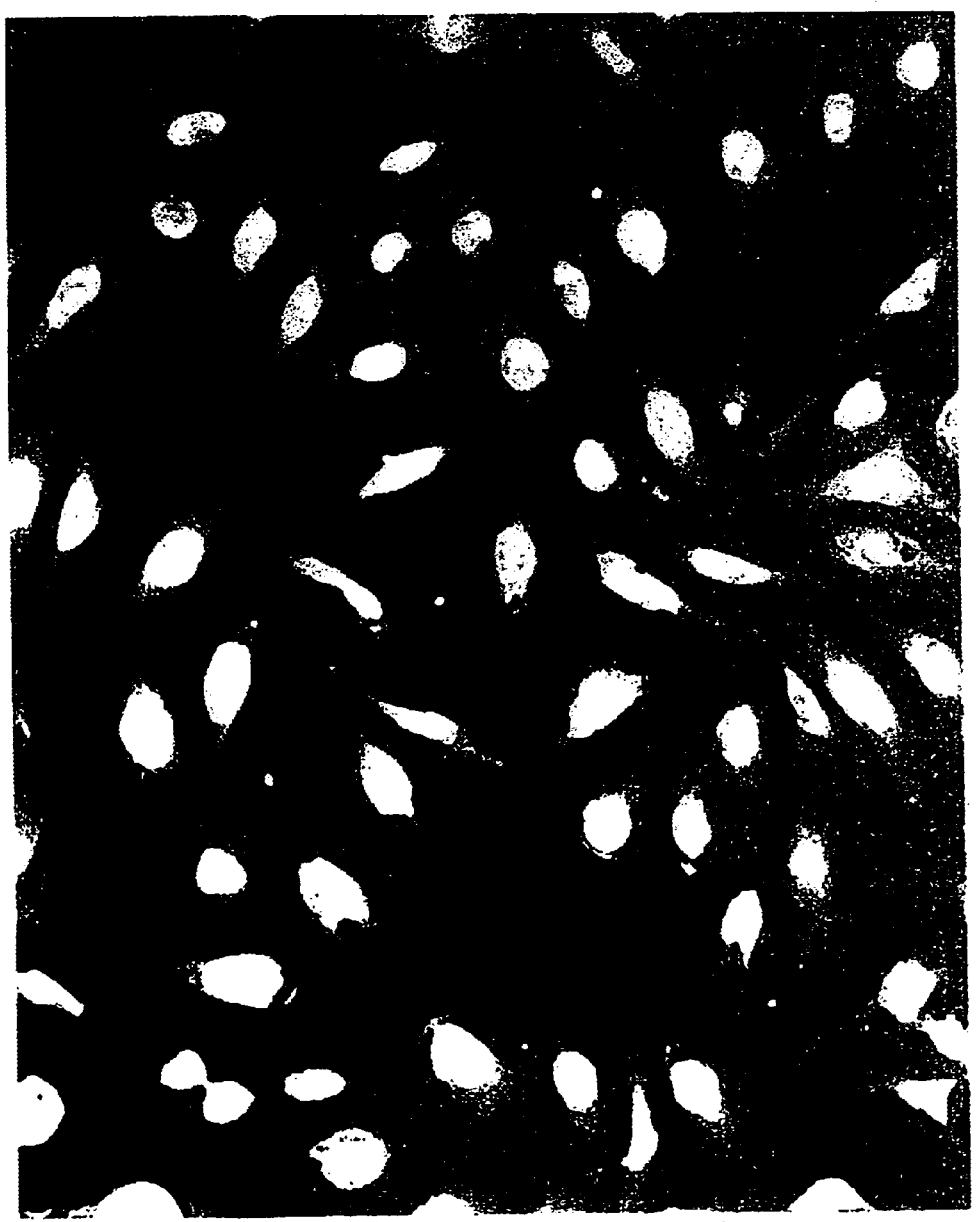
FIG. 4 is a micrograph (magnified 200×) of the sample shown in FIG. 3.
Figure 5:
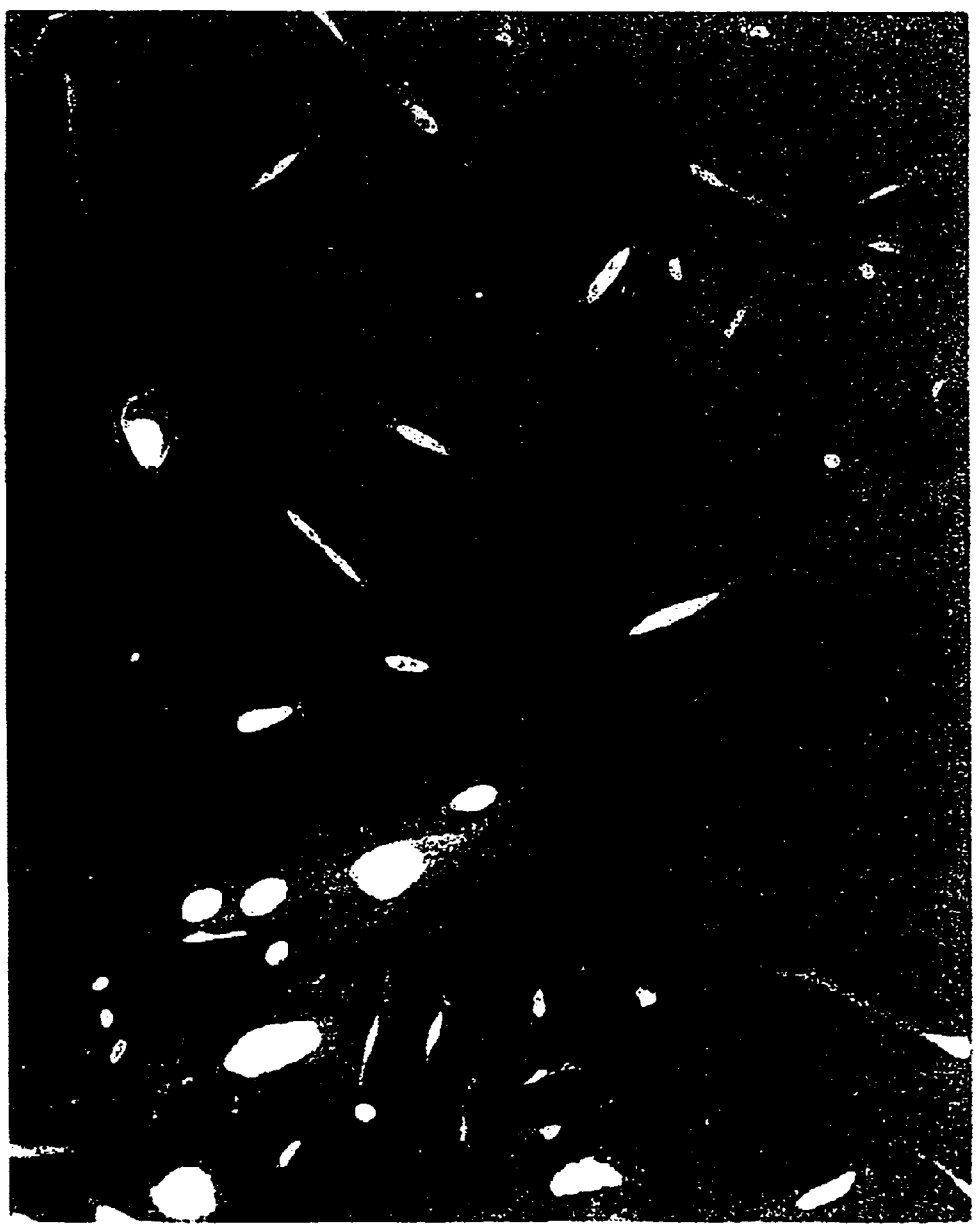
FIG. 5 is a micrograph (magnified 100×) of human aortic endothelial cells growing on a gelatin treated mechanical heart valve leaflet.
Figure 6:
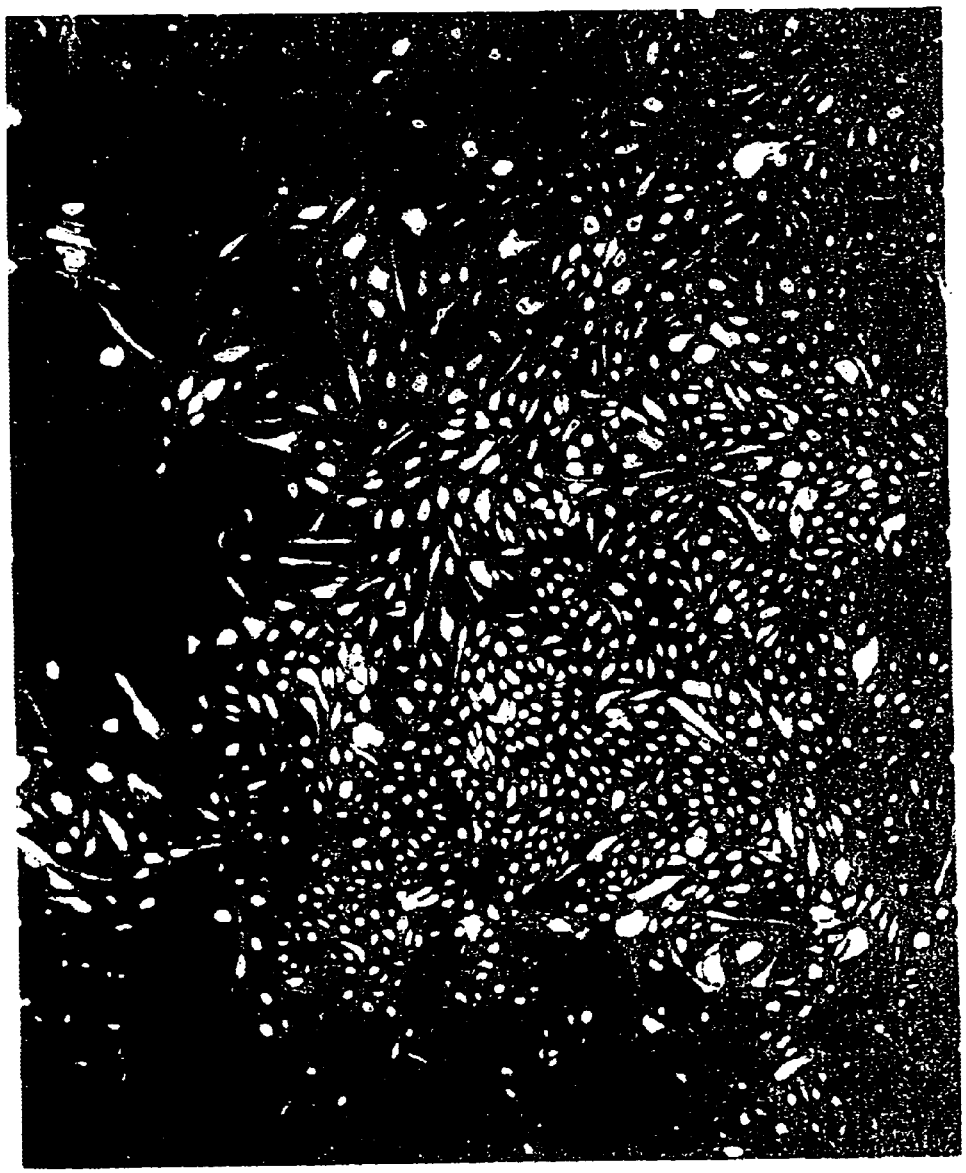
FIG. 6 is a micrograph (magnified 40×) of human aortic endothelial cells growing on a mechanical heart valve leaflet treated with both VEGF and gelatin.
Figure 7:
FIG. 7 is a micrograph (magnified 200×) of the sample shown in FIG. 6.
Figure 8:
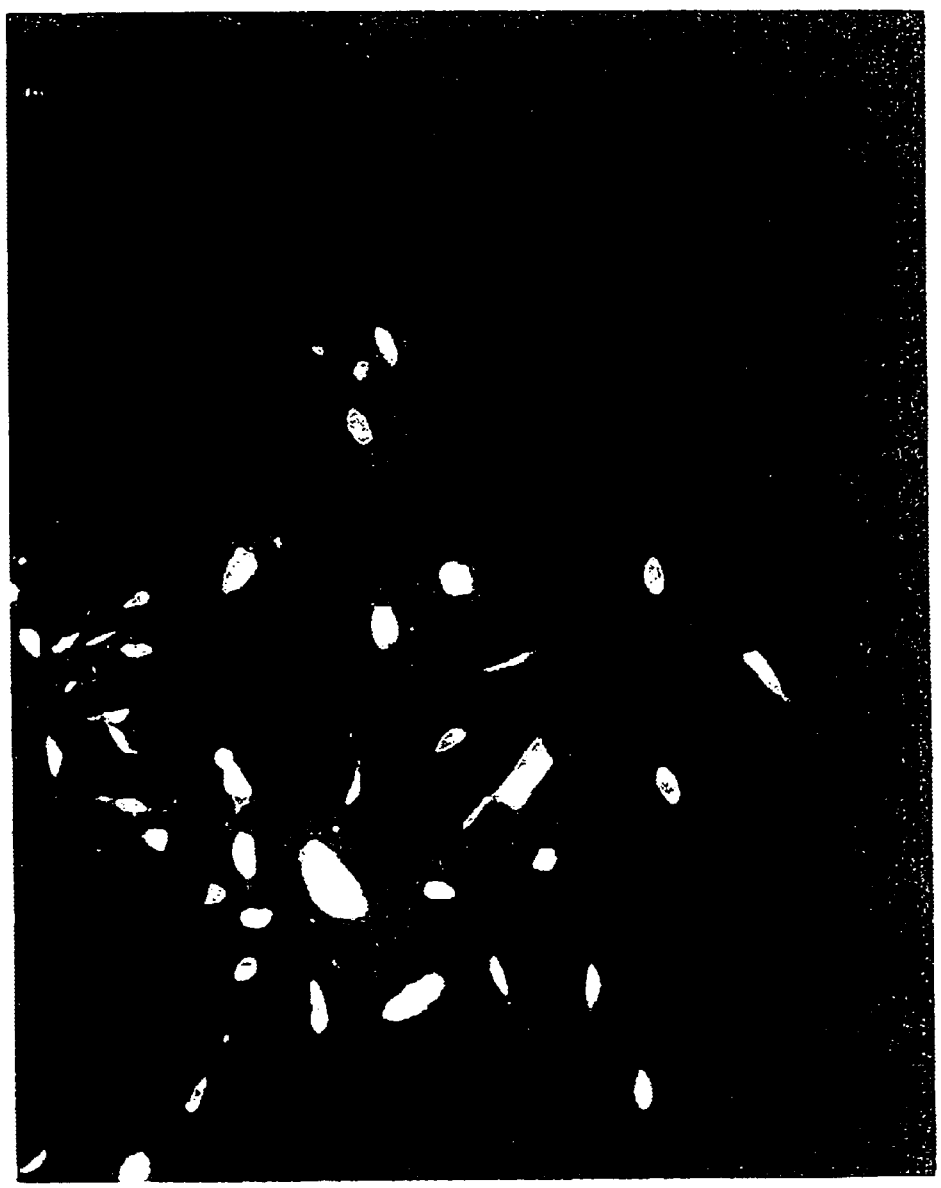
FIG. 8 is a micrograph (magnified 100×) of human aortic endothelial cells growing on a mechanical heart valve leaflet treated with extracellular matrix proteins.
Figure 9:
FIG. 9 is a micrograph (magnified 40×) of human aortic endothelial cells growing on a mechanical heart valve leaflet treated with extracellular matrix proteins and VEGF.
Figure 10:
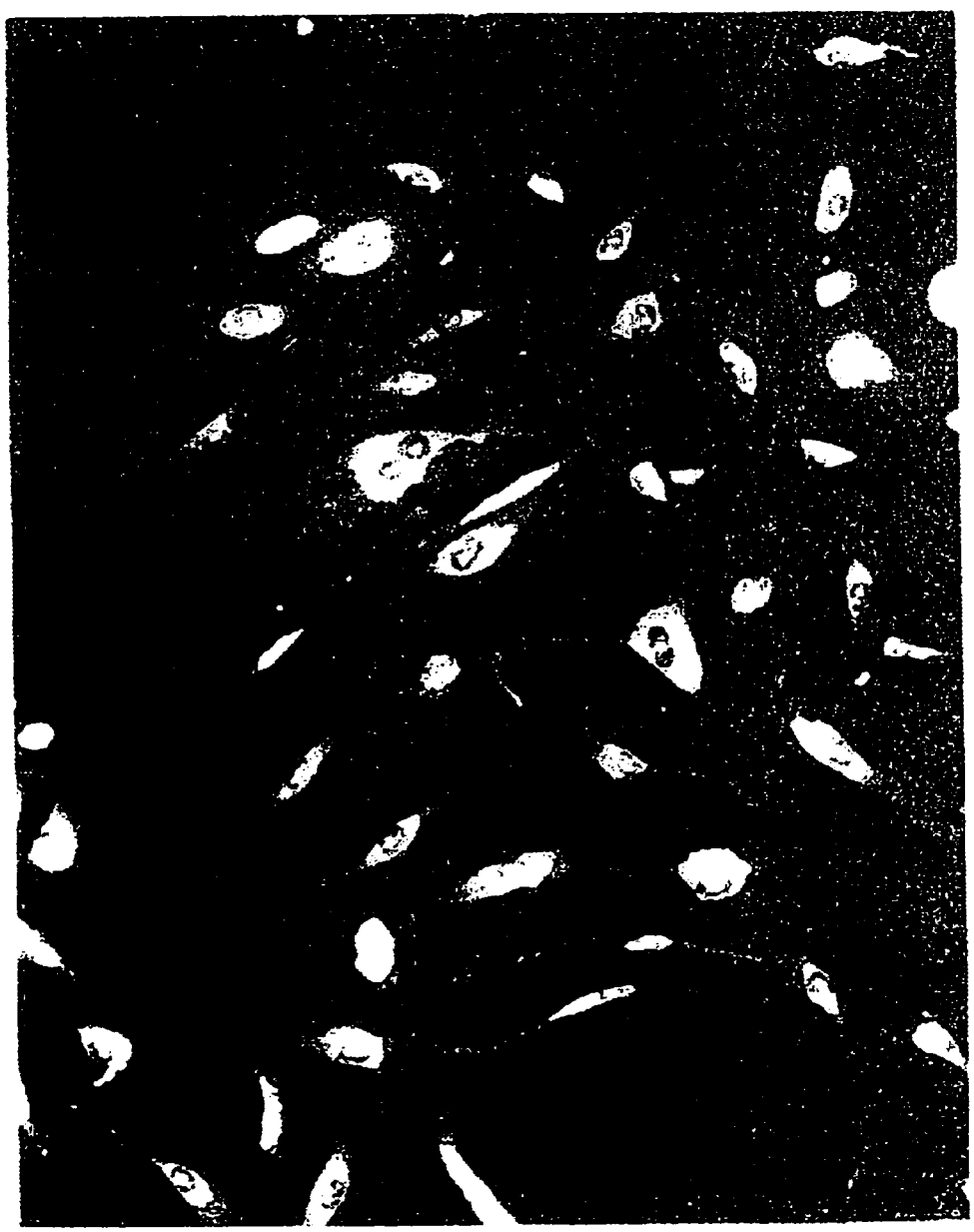
FIG. 10 is a micrograph (magnified 200×) of the sample in FIG. 9.

Samples without associated protein had no attached cells and are not shown. Results from DiI staining of cells attached to the occluder demonstrated that the pyrolytic carbon coated materials incubated with VEGF solution had very thick growths of endothelial cells colonizing the surface of the samples, as shown in FIGS. 3 (40×) and 4 (200×). The samples incubated in gelatin alone had some endothelial cell association with the pyrolytic carbon, as shown in FIG. 5, while samples incubated in both gelatin and VEGF had extensive colonization of the pyrolytic carbon surface, as shown in FIGS. 6 (40×) and 7 (200×). Similarly, samples incubated in a solution of extracellular matrix material alone had some endothelial cell association with the pyrolytic carbon, as shown in FIG. 8 (100×), while samples incubated in extracellular matrix material with VEGF exhibited more extensive growth, as shown in FIGS. 9 (40×) and 10 (100×).

Based on the Live/Dead staining results, roughly similar numbers of cells grew on occluders treated with either gelatin or gelatin+VEGF. VEGF dramatically improved the ability of the ECM gel to support endothelial cell growth. In all cases, cells seen on the surface of the occluders stained green indicating they were viable cells.

Example 3

Stimulation of Cell Adhesion by VEGF, Gelatin and Fibronectin with Vitronectin

This Example further demonstrates the ability of gelatin, and specific extracellular matrix proteins such as fibronectin and vitronectin, as well as VEGF to stimulate cell growth in association with a pyrolytic carbon coated material.

HAECs were seeded onto 36 gelatin coated 12 mm tissue culture inserts that were placed into two 24 well plates and allowed to grow to confluence as described in Example 2. Clinical grade pyrolytic carbon coated occluders were cut into 1 cm squares sectioned from leaflets using a diamond saw. These leaflet section samples were cleaned using a technique identical to that used in preparing clinical grade valve prostheses following standard manufacturing techniques. The occluder sections fit into the wells of a 24 well plate. Occluder samples were sterilized by autoclaving as described in Example 1.

Extracellular matrix solutions were prepared from sterile reagents using aseptic technique to preserve sterility. In particular, a three ml 0.1 mg/ml solution of fibronectin formed by a ten fold dilution of a 1 mg/ml stock solution (Sigma Chemicals—cat #F-0895, lot # 56H9322) was combined with 50 μg vitronectin (Sigma Chemicals—cat #V-8379, lot #67H4110). The solution of fibronectin/vitronectin (F/V) was warmed to room temperature. A 2% by weight gelatin solution such as that used to coat inserts was purchased from Sigma Chemical and warmed to 37° C. In addition, a VEGF solution was made as described in earlier examples by combining 20 ml HBSS with 4 μl 50% by volume glutaraldehyde and 200 μl of 10 μg/ml VEGF solution. A control solution was made exactly the same way but without addition of VEGF.

Twelve occluder samples were incubated in the gelatin solution and twelve occluder samples were incubated in the F/V solution at room temperature for one hour. The remaining twelve occluder samples were not incubated in any solution during this period. Then, six occluder samples from each pretreatment group (no solution, gelatin, and F/V solution) were put in one of three separate vials containing 5 ml of VEGF solution. The remaining six occluder samples from each pretreatment group were put in one of three separate vials containing 5 ml of the control solution. The twelve occluder samples were incubated in control or VEGF solution for 30 minutes at room temperature.

Both untreated and treated occluder samples were transferred to the wells of two new 24-well tissue culture plates as follows:

Wells 1–6: No extracellular matrix pretreatment, control solution (no VEGF)

Wells 7–12: No extracellular matrix pretreatment, 100 ng/ml VEGF solution

Wells 13–18: Gelatin pretreatment, control solution (no VEGF)

Wells 19–24: Gelatin pretreatment, 100 ng/ml VEGF solution

Wells 25–30: F/V pretreatment, control solution (no VEGF)

Wells 31–36: F/V pretreatment, 100 ng/ml VEGF solution

Following 30 minutes of incubation, occluder samples in each well were rinsed with sterile 0.9% saline three times and covered with 0.5 ml of growth media (EGM, Clonetic, Inc.) warmed to 37° C.

Tissue culture plates containing confluent HAECs grown on tissue culture inserts were removed from the incubator. A 5 mm diameter hole was punched in the center of each insert, as described in Example 2. The inserts were transferred to the plates containing the occluders. One insert was placed over the top of each occluder such that the edges of the hole in the center of each insert made contact with the top of the occluder. Wells were rinsed and covered with 0.5 ml fresh EGM and returned to the incubator. Cells were incubated with the occluders for a period of five days with EGM replaced every other day.

At the end of the five day period, the plates were removed. Any cells adhering to the occluders were analyzed by staining with DiI, as described in Example 1. The stained samples were imaged using a tetramethylrhodamine isothiocyanate filter and photographed.

Figure 11:
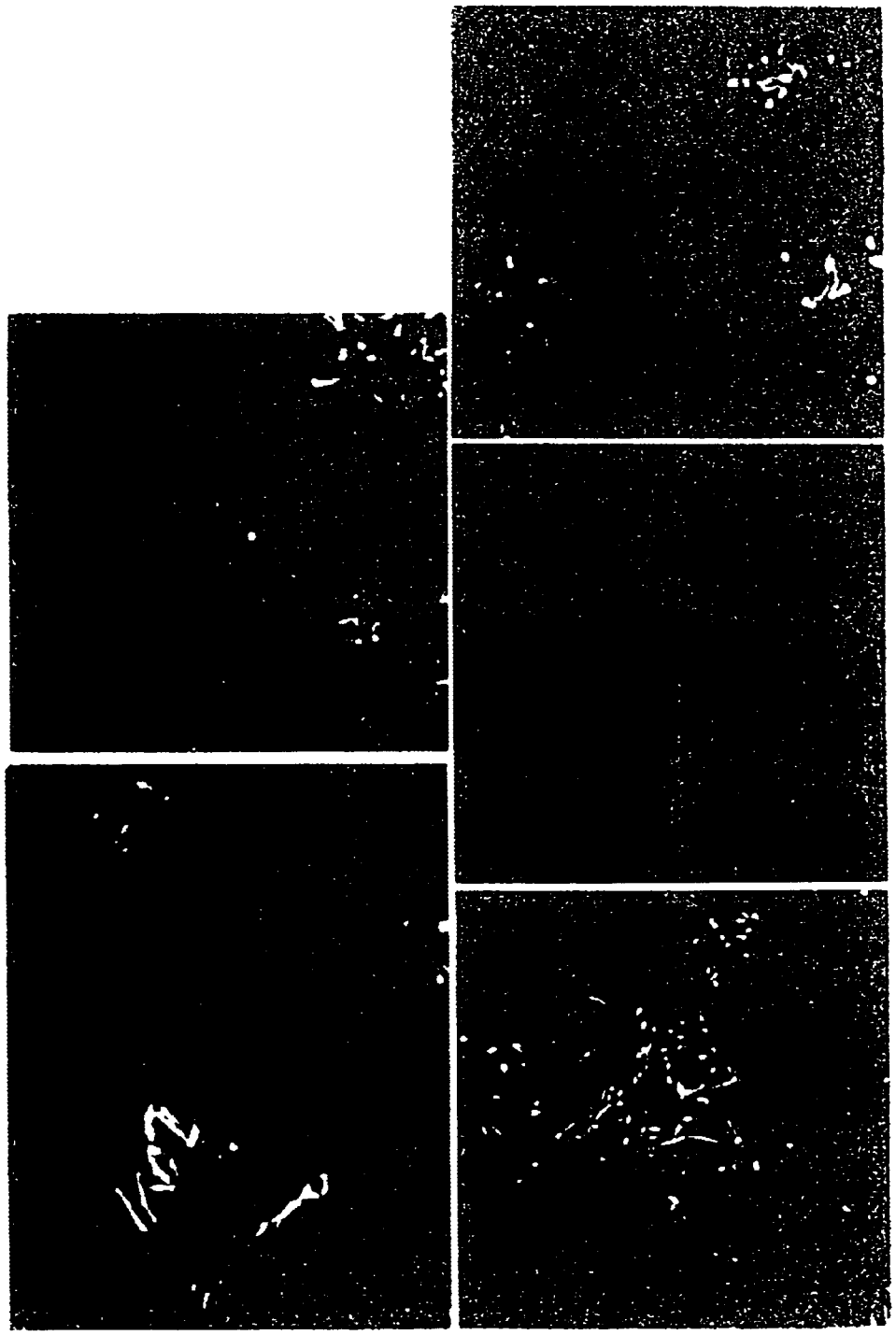
FIG. 11 is a display of five micrographs (magnified 40×) of human aortic endothelial cells growing on five pyrolytic carbon heart valve leaflets.
Figure 12:
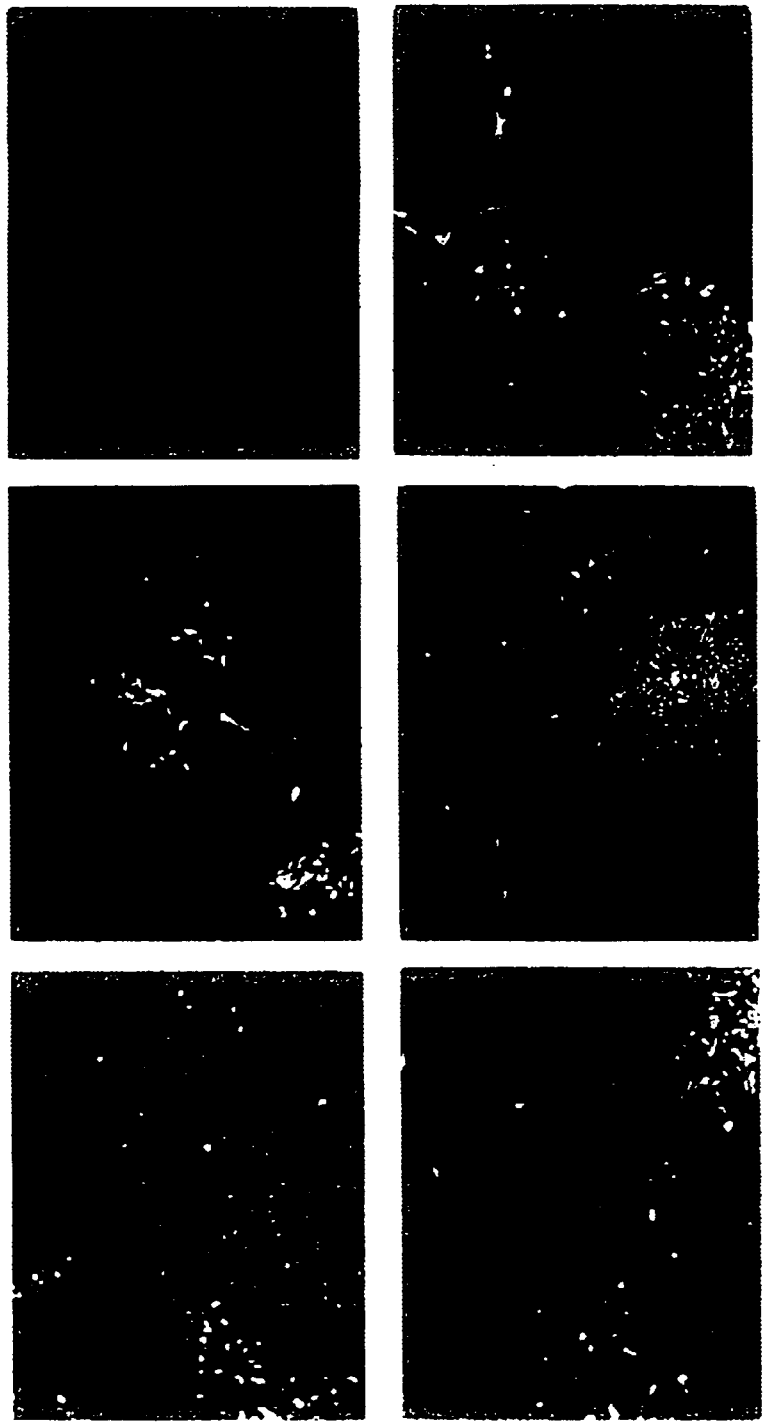
FIG. 12 is a display of six micrographs (magnified 40×) of human aortic endothelial cells growing on six VEGF treated mechanical heart valve leaflets.
Figure 16:
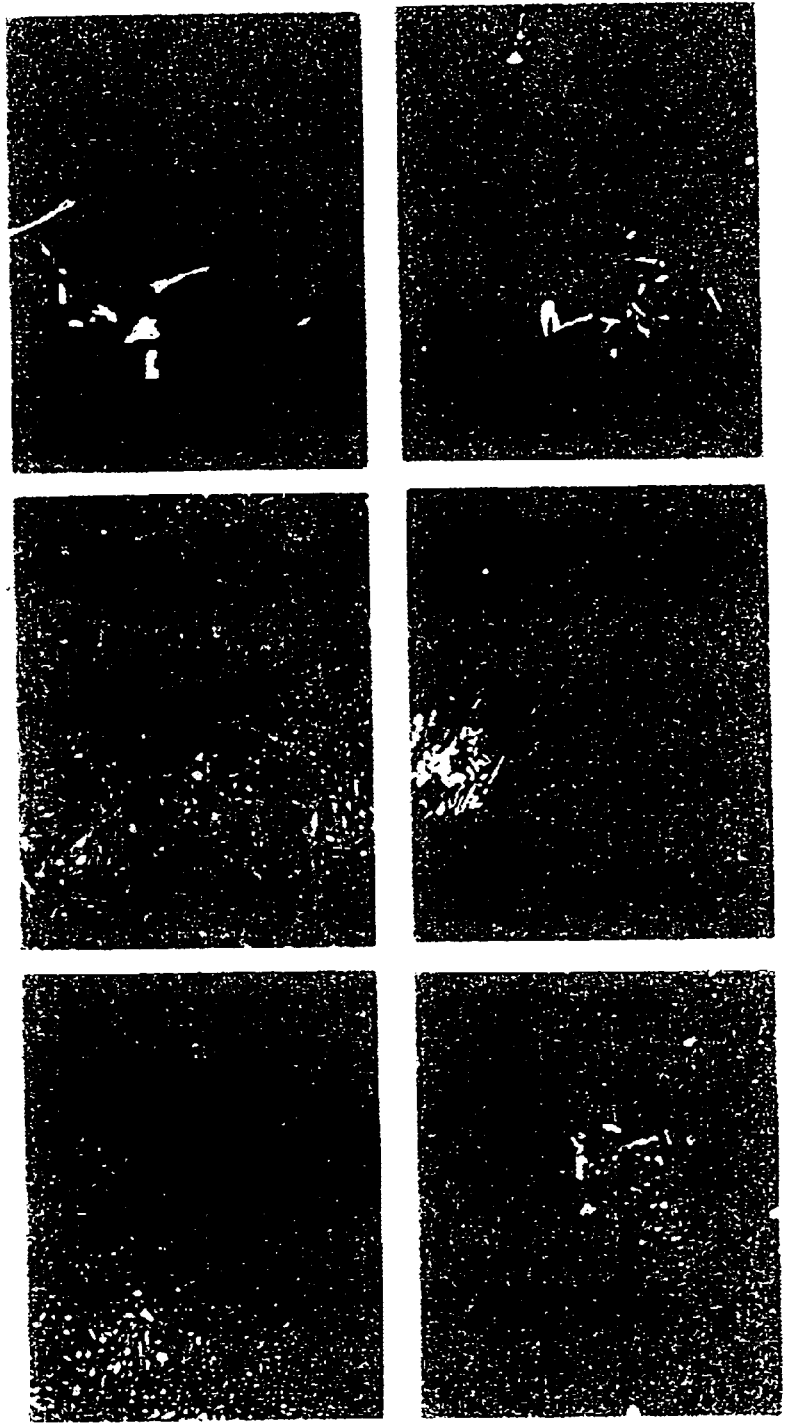
FIG. 16 is a display of six micrographs (magnified 40×) of human aortic endothelial cells growing on six mechanical heart valve leaflets treated with fibronectin and vitronectin proteins and VEGF.

In this example, samples without associated protein had some attached cells as shown in FIG. 11. The samples incubated with VEGF solution had more extensive growths of endothelial cells colonizing the surface of the pyrolytic carbon, as shown in FIG. 12. The samples incubated in gelatin alone had regions of extensive endothelial cells association with the pyrolytic carbon, as shown in FIG. 13, while samples incubated in both gelatin and VEGF had regions of significant colonization of the pyrolytic carbon surface, as shown in FIG. 14. Similarly, samples incubated in a solution of fibronectin/vitronectin alone had regions of extensive endothelial cell association with the pyrolytic carbon, as shown in FIG. 15. Furthermore, samples incubated in fibronectin/vitronectin with VEGF exhibited some regions with relatively extensive growth, as shown in FIG. 16.

The embodiments described above are intended to be illustrative and not limiting. Additional embodiments are within the claims below. Although the present invention has been described with reference to preferred embodiments, workers skilled in the art will recognize that changes may be made in form and detail without departing from the spirit and scope of the invention.

What is claimed is:

1. A medical article suitable for contacting a patient's bodily fluids comprising a biocompatible material and at least one cell adhesion stimulating protein associated with the biocompatible material, the biocompatible material comprising a ceramic material and the cell adhesion stimulating protein being selected from the group consisting of VEGF, fibroblast growth factor, Tat protein, and combinations thereof, further comprising a layer of viable cells in association with the ceramic material to reduce or inhibit thrombosis.

2. The medical article of claim 1 wherein the ceramic material comprises pyrolytic carbon.

3. The medical article of claim 1 wherein the ceramic material comprises diamond-like carbon.

4. The medical article of claim 1 wherein the cell adhesion stimulating protein further comprises a structural protein.

5. The medical article of claim 4 wherein the cell adhesion stimulating protein comprises a structural protein selected from the group consisting of gelatin, collagen, fibronectin, vitronectin and laminin.

6. The medical article of claim 4 wherein the at least one cell adhesion stimulating protein comprises a plurality of structural proteins.

7. The medical article of claim 1 wherein the cell adhesion stimulating protein comprises vascular endothelial growth factor.

8. The medical article of claim 7 wherein the vascular endothelial growth factor is selected from the group consisting of $hVEGF_{165}$, $hVEGF_{121}$, VEGF II, $hVEGF_{728}$, VEGF2, and VEGF-B.

9. The medical article of claim 7 wherein the vascular endothelial growth factor is selected from the group consisting of polypeptide fragments of natural vascular endothelial growth factor proteins, chemically modified VEGF proteins and recombinant modified VEGF polypeptides.

10. The medical article of claim 1 wherein the cell adhesion stimulating protein comprises Tat protein.

11. The medical article of claim 1 wherein the medical article comprises an artificial organ, a heart valve prosthesis, an annuloplasty ring, a stent, a pledget, suture, an electrical lead, a permanently in-dwelling percutaneous device, an AV shunt, a vascular graft, a dermal graft or a surgical patch.

12. The medical article of claim 1 wherein the medical article comprises a heart valve prosthesis comprising an occluder and the ceramic comprises pyrolytic carbon deposited on the occluder.

13. A method for producing a medical article suitable for contact with a patient's bodily fluids, the method comprising:

inducing the colonization and proliferation of viable cells to reduce or inhibit thrombosis by adhering a cell adhesion stimulating protein to a ceramic material, the cell adhesion stimulating protein being selected from the group consisting of VEGF, fibroblast growth factor, and combinations thereof.

14. The method of claim 13 wherein the adhering of the cell adhesion stimulating protein to the ceramic material is performed using an adhesive.

15. The method of claim 13 wherein the cell adhesion stimulating protein further comprises a structural protein.

16. The method of claim 15 wherein the structural protein comprises gelatin.

17. The method of claim 15 wherein the structural protein comprises an extracellular matrix component.

18. The method of claim 15 wherein the structural protein comprises collagen.

19. The method of claim 13 wherein the cell adhesion stimulating protein comprises vascular endothelial growth factor.

20. The method of claim 13 wherein the cell adhesion stimulating protein comprises a structural protein and the method further comprises adhering a growth factor to the ceramic material.

21. The method of claim 13 further comprising contacting the ceramic material having an adhered cell adhesion stimulating protein with viable cells in a cell culture to associate the viable cells with the ceramic material.

22. The method of claim 21 wherein the cell adhesion stimulating protein comprises vascular endothelial growth factor and the viable cells comprise human endothelial cells.

23. A method for producing a prosthesis comprising:

harvesting viable cells from a patient;

adhering a cell adhesion stimulating protein comprising a growth factor to a ceramic material; and associating the viable cells with the ceramic material by contacting the ceramic material having adhered said cell adhesion stimulating protein with a cell culture comprising the viable cells.

24. The method of claim 23 comprising attaching said cell adhesion stimulating protein to the ceramic material using a material selected from the group consisting of binders, adhesives and mixtures thereof.

25. The method of claim 23 comprising attaching said cell adhesion stimulating protein to the ceramic material using chemical bonding.

26. A method for producing a prosthesis comprising:

harvesting viable cells from a patient;

adhering a cell adhesion stimulating protein to a ceramic material; and associating the viable cells with the ceramic material by contacting the ceramic material having adhered said cell adhesion stimulating protein with a cell culture comprising the viable cells;

wherein the viable cells comprise endothelial cells, the cell adhesion stimulating protein comprises vascular endothelial growth factor and the ceramic material comprises pyrolytic carbon.

27. The method of claim 26 further comprising assembling a heart valve prosthesis wherein the occluder of the heart valve prosthesis comprises the ceramic material with associated viable cells.

28. A medical article suitable for contacting a patient's bodily fluids comprising a biocompatible material and at least one cell adhesion stimulating protein associated with the biocompatible material, the biocompatible material comprising a ceramic material and the cell adhesion stimulating protein comprising a structural protein and a growth factor, further comprising a layer of viable cells in association with the ceramic material to reduce or inhibit thrombosis.

29. The medical article of claim 28 wherein the ceramic material comprises pyrolytic carbon.

30. The medical article of claim 28 wherein the structural protein is a member of the group consisting of gelatin, collagen, fibronectin, vitronectin, and laminin.

31. The medical article of claim 28 wherein the growth factor is chosen from the group consisting of VEGF, fibroblast growth factor, and Tat protein.

32. The medical article of claim 28 wherein the growth factor comprises VEGF.

33. A method for producing a medical article suitable for contact with a patient's bodily fluids, the method comprising:

inducing the colonization and proliferation of viable cells to reduce or inhibit thrombosis by adhering a cell adhesion stimulating protein to a ceramic material, the cell adhesion stimulating protein comprising a structural protein and a growth factor.

34. The method of claim 33 further comprising contacting the ceramic material having an adhered cell adhesion stimulating protein with viable cells in a cell culture to associate the viable cells with the ceramic material.

35. The method of claim 33 wherein the growth factor comprises VEGF.

* * * * *